US011389783B2

(12) United States Patent
Gu

(10) Patent No.: US 11,389,783 B2
(45) Date of Patent: Jul. 19, 2022

(54) FUNCTIONALIZED SUPPORT MATERIAL AND METHODS OF MAKING AND USING FUNCTIONALIZED SUPPORT MATERIAL

(71) Applicant: W.R. Grace & Co.-Conn., Columbia, MD (US)

(72) Inventor: Feng Gu, Ellicott City, MD (US)

(73) Assignee: W.R. GRACE & CO.-CONN., Columbia, MD (US)

( * ) Notice: Subject to any disclaimer, the term of this patent is extended or adjusted under 35 U.S.C. 154(b) by 65 days.

(21) Appl. No.: 15/308,241

(22) PCT Filed: Apr. 30, 2015

(86) PCT No.: PCT/US2015/028476
§ 371 (c)(1),
(2) Date: Nov. 1, 2016

(87) PCT Pub. No.: WO2015/168383
PCT Pub. Date: Nov. 5, 2015

(65) Prior Publication Data
US 2017/0056854 A1 Mar. 2, 2017

Related U.S. Application Data

(60) Provisional application No. 61/987,938, filed on May 2, 2014.

(51) Int. Cl.
| | | |
|---|---|---|
| *B01J 20/32* | (2006.01) | |
| *B01J 39/26* | (2006.01) | |
| *B01J 41/20* | (2006.01) | |
| *B01J 20/289* | (2006.01) | |
| *B01J 41/05* | (2017.01) | |
| *B01J 39/17* | (2017.01) | |
| *B01J 39/05* | (2017.01) | |
| *B01D 15/36* | (2006.01) | |
| *C07K 1/18* | (2006.01) | |

(52) U.S. Cl.
CPC ........ *B01J 20/3272* (2013.01); *B01D 15/362* (2013.01); *B01D 15/363* (2013.01); *B01J 20/289* (2013.01); *B01J 20/3204* (2013.01); *B01J 20/3219* (2013.01); *B01J 39/05* (2017.01); *B01J 39/17* (2017.01); *B01J 39/26* (2013.01); *B01J 41/05* (2017.01); *B01J 41/20* (2013.01); *C07K 1/18* (2013.01)

(58) Field of Classification Search
None
See application file for complete search history.

(56) References Cited

U.S. PATENT DOCUMENTS

| | | | |
|---|---|---|---|
| 3,505,785 A | 4/1970 | Kirkland | |
| 3,526,603 A | 9/1970 | Acker | B01J 11/36 |
| 3,652,216 A | 3/1972 | Krekeler et al. | 23/162 |
| 3,782,075 A | 1/1974 | Kirkland | 55/67 |
| 3,855,172 A | 12/1974 | Iler et al. | 260/39 R |
| 3,869,409 A | 3/1975 | Bebris et al. | 262/446 |
| 3,888,972 A | 6/1975 | Kiselev et al. | 423/338 |
| 3,904,598 A | 9/1975 | Isaac | 260/210.5 |
| 3,943,072 A | 3/1976 | Thomson et al. | 252/465 R |
| 3,956,179 A | 5/1976 | Sebastian et al. | 252/430 |
| 3,975,293 A | 8/1976 | LePage | 252/317 |
| 3,984,349 A | 10/1976 | Meiler et al. | 252/428 |
| 4,010,242 A | 3/1977 | Iler et al. | 423/335 |
| 4,029,583 A | 5/1977 | Ho Chang et al. | 252/184 |
| 4,034,139 A | 7/1977 | Mazarguil et al. | 428/405 |
| 4,061,828 A | 12/1977 | Mazarguil et al. | 428/403 |
| 4,070,286 A | 1/1978 | Iler et al. | 210/31 C |
| 4,076,651 A | 2/1978 | Jacques | 252/461 |
| 4,100,149 A | 7/1978 | Meiller et al. | 260/112 R |
| 4,104,363 A | 8/1978 | Vozka et al. | 423/338 |
| 4,118,316 A | 10/1978 | Talley et al. | 210/31 C |
| 4,124,699 A | 11/1978 | Michel et al. | 423/628 |
| 4,131,542 A | 12/1978 | Bergna et al. | 210/31 |
| 4,140,653 A | 2/1979 | Imura et al. | 252/430 |
| 4,157,920 A | 6/1979 | Wason et al. | 108/292 |
| 4,168,216 A | 9/1979 | Burkhardt et al. | 204/98 |
| 4,170,685 A | 10/1979 | Rembaum et al. | 428/402 |

(Continued)

FOREIGN PATENT DOCUMENTS

| | | | |
|---|---|---|---|
| CA | 1303594 C | 6/1992 | |
| CA | 2564413 | 12/2005 | B01J 20/28 |

(Continued)

OTHER PUBLICATIONS

Bach, Long Giang; Islam, Md. Rafiqul; Jeong, Yeon Tae; Hwang, Ha Soo; Lim, Kwon Taek, "A Facile Synthesis of PMMA-SiO2 Nanocomposites via Surface Initiated Radical Polymerization", Molecular Crystals and Liquid Crystals, 565(1), 78-87 (2012).

Banerjee, Jaya; Kumar, Rajesh; Srivastava, Abhishek; Behari, Kunj, "Graft Copolymerization of 2-Acrylamido-2-Methyl-1-Propanesulfonic Acid onto Carboxymethylcellulose (Sodium Salt) Using Bromate/Thiourea Redox Pair", Journal of Applied Polymer Science, 100(1), 26-34 (2006).

Bowes, Brian D, "Protein Transport and Adsorption in Polymer-Modified Ion-Exchange Media", University of Delaware, ProQuest Dissertations Publishing (2011).

Breadmore, Michael C.; Shrinivasan, Sushil; Karlinsey, James; Ferrance, Jerome P.; Norris, Pamela M.; Landers, James P. "Towards a Microchip-Based Chromatographic Platform. Part 2: Sol-Gel Phases Modified with Polyelectrolyte Multilayers for Capillary Electrochromatography", Electrophoresis, v 24, p. 1261-1270 (2003).

(Continued)

*Primary Examiner* — Ryan B Huang
(74) *Attorney, Agent, or Firm* — Foley & Lardner LLP

(57) ABSTRACT

Methods of making functionalized support material are disclosed. Functionalized support material suitable for use in chromatography columns or cartridges, such as in a high pressure liquid chromatography (HPLC) column or a fast protein liquid chromatography (FPLC) column, is also disclosed. Chromatography columns or cartridges containing the functionalized support material, and methods of using functionalized support material, such as a media (e.g., chromatographic material) in a chromatography column or cartridge, are also disclosed.

28 Claims, 2 Drawing Sheets

(56) References Cited

U.S. PATENT DOCUMENTS

| | | | |
|---|---|---|---|
| 4,229,342 A | 1/1980 | Mirabel | 260/120 |
| 4,199,450 A | 4/1980 | Dulout et al. | 210/31 |
| 4,275,300 A | 6/1981 | Abbott | 250/304 |
| 4,298,500 A | 11/1981 | Abbott | 252/428 |
| 4,308,254 A | 12/1981 | Tayot et al. | 424/134 |
| 4,322,542 A | 3/1982 | Abbott | 566/425 |
| 4,329,434 A | 5/1982 | Kimoto et al. | 521/27 |
| 4,329,435 A | 5/1982 | Kimoto et al. | 521/38 |
| 4,376,140 A | 3/1983 | Kimoto et al. | 427/244 |
| 4,397,827 A | 8/1983 | Chu | 423/326 |
| 4,415,631 A | 11/1983 | Schutijser | |
| 4,496,461 A | 1/1985 | Leeke et al. | 210/198.2 |
| 4,517,131 A | 5/1985 | Hefner, Jr. | 260/465 F |
| 4,532,232 A | 7/1985 | Larsson et al. | |
| 4,536,352 A | 8/1985 | Kimoto et al. | 260/543 |
| 4,540,486 A | 9/1985 | Ramsden | 210/198.2 |
| 4,551,245 A | 11/1985 | Ramsden et al. | 210/198.2 |
| 4,569,917 A | 2/1986 | Maier et al. | 436/71 |
| 4,576,927 A * | 3/1986 | Kuroda | B01J 20/3204 502/401 |
| 4,581,428 A | 4/1986 | Farnham et al. | 526/190 |
| 4,597,913 A | 7/1986 | Kimoto et al. | 558/436 |
| 4,606,825 A | 8/1986 | Crane et al. | 210/635 |
| 4,639,513 A | 1/1987 | Hou et al. | 630/387 |
| 4,640,909 A | 2/1987 | Ramsden et al. | 502/407 |
| 4,648,975 A | 3/1987 | Barkatt et al. | 210/656 |
| 4,650,784 A | 3/1987 | Ramsden et al. | 502/407 |
| 4,661,248 A | 4/1987 | Ramsden et al. | 210/198.2 |
| 4,673,734 A | 6/1987 | Tayot et al. | 530/364 |
| 4,676,898 A | 6/1987 | Saxena | 210/198.2 |
| 4,699,717 A | 10/1987 | Riesner et al. | 210/635 |
| 4,704,374 A | 11/1987 | Jacques | 502/8 |
| 4,724,207 A | 2/1988 | Hou et al. | 435/180 |
| 4,724,210 A | 2/1988 | Oka et al. | 435/239 |
| 4,732,887 A | 3/1988 | Obanawa et al. | 502/402 |
| 4,740,298 A | 4/1988 | Andresen et al. | 210/198.3 |
| 4,745,097 A | 5/1988 | Maekawa et al. | 503/209 |
| 4,746,572 A | 5/1988 | Glajch et al. | 428/403 |
| 4,756,834 A | 7/1988 | Muller et al. | 210/635 |
| 4,780,423 A | 10/1988 | Bluestein et al. | 436/527 |
| 4,783,264 A | 11/1988 | Nylen et al. | 210/638 |
| 4,851,382 A | 7/1989 | Kusano et al. | 502/401 |
| 4,855,054 A | 8/1989 | Williams | 210/638 |
| 4,895,806 A | 1/1990 | Le et al. | 435/288 |
| 4,917,781 A | 4/1990 | Shariffan et al. | 204/72 |
| 4,923,978 A | 5/1990 | McCormick | 536/27 |
| 4,950,634 A | 8/1990 | Williams et al. | 502/401 |
| 4,956,180 A | 9/1990 | Cassani et al. | 424/118 |
| 4,959,340 A | 9/1990 | Williams | B01J 20/22 |
| 4,990,456 A | 2/1991 | Loucks et al. | 436/139 |
| 5,004,688 A | 4/1991 | Craig et al. | 436/58.3 |
| 5,009,688 A | 4/1991 | Nakanishi | 55/18.3 |
| 5,030,286 A | 7/1991 | Crawford et al. | 106/435 |
| 5,032,266 A | 7/1991 | Kirkland et al. | 210/198.2 |
| 5,035,803 A | 7/1991 | Cohen | 210/656 |
| 5,057,426 A | 10/1991 | Henco et al. | 435/270 |
| 5,059,654 A | 10/1991 | Hou et al. | |
| 5,085,779 A | 2/1992 | Crane et al. | 210/638 |
| 5,087,359 A | 2/1992 | Kakodkar et al. | 210/198.2 |
| 5,091,433 A | 2/1992 | Wulff et al. | 521/54 |
| 5,092,992 A | 3/1992 | Crane et al. | 210/198.2 |
| 5,099,923 A | 3/1992 | Aften et al. | 168/294 |
| 5,128,291 A | 7/1992 | Wax et al. | 502/8 |
| 5,141,806 A | 8/1992 | Koontz | 428/316.5 |
| 5,149,425 A | 9/1992 | Mazid et al. | 210/198.2 |
| 5,149,553 A | 9/1992 | Berg | 426/330.4 |
| 5,151,350 A | 9/1992 | Colbert et al. | 435/69.1 |
| 5,152,906 A | 10/1992 | Aften et al. | 252/8.551 |
| 5,190,660 A | 3/1993 | Lindoy et al. | 210/670 |
| 5,190,844 A | 3/1993 | Yabuuchi et al. | 430/137 |
| 5,203,991 A | 4/1993 | Kutsuna et al. | 210/198.2 |
| 5,230,833 A | 7/1993 | Romberger et al. | 252/383.5 |
| 5,268,097 A | 12/1993 | Girot et al. | 502/402 |
| 5,318,848 A | 6/1994 | Itoh et al. | 428/405 |
| 5,354,548 A | 10/1994 | Araya et al. | 423/700 |
| 5,372,820 A | 12/1994 | Jozefonvicz nee Dorgebray et al. | 424/499 |
| 5,380,706 A | 1/1995 | Himes et al. | 507/129 |
| 5,401,809 A | 3/1995 | Gitzel et al. | 525/387 |
| 5,431,807 A | 7/1995 | Frechet et al. | 210/198.2 |
| 5,447,859 A | 9/1995 | Prussak | 435/239 |
| 5,451,660 A | 9/1995 | Builder et al. | 530/344 |
| 5,453,186 A * | 9/1995 | Muller | B01D 15/08 210/198.2 |
| 5,468,847 A | 11/1995 | Heilmann et al. | 530/413 |
| 5,480,542 A | 1/1996 | Asakawa et al. | 210/198.2 |
| 5,510,394 A | 4/1996 | Hodgdon | 521/27 |
| 5,512,169 A | 4/1996 | Williams | 210/198.2 |
| 5,593,576 A | 1/1997 | Girot et al. | 210/198.2 |
| 5,593,757 A | 1/1997 | Kashiwazaki et al. | 428/195 |
| 5,610,274 A | 3/1997 | Wong | 530/334 |
| 5,622,743 A | 4/1997 | Tanaka et al. | |
| 5,624,875 A | 4/1997 | Nakanishi et al. | 501/39 |
| 5,633,290 A | 5/1997 | Frechet et al. | 521/54 |
| 5,652,348 A | 7/1997 | Burton et al. | 536/20 |
| 5,674,932 A | 10/1997 | Agostini et al. | 524/430 |
| 5,701,956 A | 12/1997 | Hardy et al. | 166/295 |
| 5,707,516 A | 1/1998 | Tomizawa et al. | 210/198.2 |
| 5,710,264 A | 1/1998 | Urdea et al. | 536/23.1 |
| 5,759,405 A | 6/1998 | Anderson et al. | 210/656 |
| 5,805,264 A | 9/1998 | Janssen et al. | 351/160 R |
| 5,808,041 A | 9/1998 | Padhye et al. | 536/25.4 |
| 5,856,379 A | 1/1999 | Shiratsuchi et al. | |
| 5,861,134 A | 1/1999 | Swanson | 423/335 |
| 5,888,397 A | 3/1999 | Rogers et al. | 210/634 |
| 5,904,848 A | 5/1999 | Wong et al. | 210/500.36 |
| 5,906,747 A | 5/1999 | Coffman et al. | 210/635 |
| 5,911,963 A | 6/1999 | Krivak et al. | 423/335 |
| 5,914,044 A | 6/1999 | Lindoy et al. | 210/670 |
| 5,922,449 A | 7/1999 | Revis | 428/306.6 |
| 5,945,525 A | 8/1999 | Uematsu et al. | 538/25.42 |
| 5,948,894 A | 9/1999 | Berry et al. | 530/391.1 |
| 5,968,652 A | 10/1999 | Hanggi et al. | 428/405 |
| 5,970,915 A | 10/1999 | Schlueter et al. | 119/171 |
| 5,973,068 A * | 10/1999 | Yamaya | C08F 283/122 524/506 |
| 5,976,479 A | 11/1999 | Alcaraz et al. | 423/335 |
| 6,027,945 A | 2/2000 | Smith et al. | 436/528 |
| 6,037,465 A | 3/2000 | Hillebrand et al. | 538/25.42 |
| 6,043,354 A | 3/2000 | Hillebrand et al. | 538/25.42 |
| 6,074,555 A | 6/2000 | Boos et al. | 210/198.2 |
| 6,090,288 A | 7/2000 | Berglund et al. | |
| 6,127,526 A | 10/2000 | Blank et al. | 530/413 |
| 6,168,773 B1 | 1/2001 | Sharp et al. | 423/338 |
| 6,171,486 B1 | 1/2001 | Green et al. | 210/198.2 |
| 6,204,306 B1 | 3/2001 | Chabrecek et al. | 523/106 |
| 6,248,911 B1 | 6/2001 | Canessa et al. | 554/191 |
| 6,284,470 B1 | 9/2001 | Bitner et al. | 435/6 |
| 6,310,199 B1 | 10/2001 | Smith et al. | 536/25.4 |
| 6,355,726 B1 | 3/2002 | Doemling et al. | 525/54.1 |
| 6,362,320 B1 | 3/2002 | Park et al. | 530/412 |
| 6,372,353 B2 | 4/2002 | Karger et al. | 428/447 |
| 6,376,194 B2 | 4/2002 | Smith et al. | 435/6 |
| 6,379,500 B2 | 4/2002 | Greenwood et al. | 162/181.6 |
| 6,383,990 B1 | 5/2002 | Dawson et al. | 507/209 |
| 6,387,974 B1 | 5/2002 | Deissler et al. | 521/150 |
| 6,426,315 B1 | 7/2002 | Bergstrom et al. | |
| 6,428,707 B1 | 8/2002 | Berg et al. | 210/561 |
| 6,435,012 B2 | 8/2002 | Maikner et al. | 73/61.52 |
| 6,472,486 B2 | 10/2002 | Klaerner et al. | 526/220 |
| 6,482,324 B2 | 11/2002 | Kirkland et al. | 210/656 |
| 6,488,855 B2 | 12/2002 | Gjerde et al. | 210/635 |
| 6,497,964 B2 | 12/2002 | Matsumura et al. | 428/447 |
| 6,512,060 B1 | 1/2003 | Matyjaszewski et al. | 528/111 |
| 6,537,793 B2 | 3/2003 | Blanche et al. | 435/239 |
| 6,555,151 B2 | 4/2003 | Hu et al. | 428/422 |
| 6,565,905 B1 | 5/2003 | Ito et al. | 426/330.4 |
| 6,569,910 B1 | 5/2003 | Spindler et al. | 521/30 |
| 6,596,843 B2 | 7/2003 | Brunelle et al. | 528/466 |
| 6,620,326 B1 | 9/2003 | Lihme et al. | 210/635 |
| 6,624,205 B2 | 9/2003 | Muranaka | 521/25 |
| 6,632,848 B2 | 10/2003 | Sugaya | 521/27 |
| 6,649,572 B2 | 11/2003 | Dawson et al. | 507/209 |
| 6,797,814 B2 | 9/2004 | Blank | 530/413 |

(56) References Cited

U.S. PATENT DOCUMENTS

| | | | |
|---|---|---|---|
| 6,802,966 B2 | 10/2004 | Wormsbecher | 210/198.2 |
| 6,818,259 B1 | 11/2004 | Koontz | 427/562 |
| 6,852,009 B2 | 2/2005 | Kawase et al. | 431/36 |
| 6,861,103 B2 | 3/2005 | Chang et al. | 427/522 |
| 6,911,192 B2 | 6/2005 | Nakanishi | 423/338 |
| 6,916,536 B1 | 7/2005 | Hammen et al. | 428/407 |
| 6,949,613 B2 | 9/2005 | Haddleton | 526/90 |
| 6,972,090 B2 | 12/2005 | Boschetti et al. | 210/198.2 |
| 6,994,791 B2 | 2/2006 | Muller et al. | 210/656 |
| 6,994,964 B1 | 2/2006 | Chang et al. | 435/8 |
| 6,998,040 B2 | 2/2006 | Malik et al. | 210/198.2 |
| 6,998,042 B2 | 2/2006 | Wormsbecher | 210/198.2 |
| 7,008,542 B2 | 3/2006 | Belew et al. | |
| 7,012,044 B2 | 3/2006 | Dawson et al. | 507/211 |
| 7,015,281 B2 | 3/2006 | Britsch et al. | 525/61 |
| 7,033,505 B2 | 4/2006 | Urano | 210/656 |
| 7,067,059 B2 | 6/2006 | Maloisel | 210/656 |
| 7,074,491 B2 | 7/2006 | Liu et al. | 438/447 |
| 7,078,224 B1 | 7/2006 | Bitner et al. | 435/270 |
| 7,125,488 B2 | 10/2006 | Li | 210/198.2 |
| 7,128,884 B2 | 10/2006 | Kirkland et al. | 423/335 |
| 7,166,213 B2 | 1/2007 | Wormsbecher | 210/198.2 |
| 7,192,560 B2 | 3/2007 | Parthasarathy et al. | 422/101 |
| 7,198,855 B2 | 4/2007 | Liebmann-Vinson et al. | 428/447 |
| 7,220,703 B2 | 5/2007 | Hammen et al. | 602/406 |
| 7,229,655 B2 | 6/2007 | Hu et al. | 426/422 |
| 7,250,214 B2 | 7/2007 | Walter et al. | 428/405 |
| 7,250,253 B1 | 7/2007 | Klapproth et al. | 435/6 |
| 7,316,919 B2 | 1/2008 | Childs et al. | 435/177 |
| 7,318,900 B2 | 1/2008 | DeMarco | 210/656 |
| 7,323,347 B2 | 1/2008 | Quinn | 436/518 |
| 7,329,386 B2 | 2/2008 | Kobayashi et al. | 422/70 |
| 7,332,327 B2 | 2/2008 | Vikholm et al. | 435/287.2 |
| 7,338,768 B1 | 3/2008 | Trau et al. | 435/7.1 |
| 7,374,684 B2 | 5/2008 | Gibson et al. | 210/636 |
| 7,375,168 B2 | 5/2008 | Zhang et al. | 525/474 |
| 7,378,479 B2 | 5/2008 | Tamareselvy et al. | 526/333 |
| 7,390,403 B2 | 6/2008 | Siwak | 210/198.2 |
| 7,396,561 B2 | 7/2008 | Ruhe | 427/214 |
| 7,456,276 B2 | 11/2008 | Christensen et al. | 536/123.1 |
| 7,476,474 B2 | 1/2009 | Ganguli et al. | 430/5 |
| 7,479,223 B2 | 1/2009 | DiLeo et al. | 210/198.2 |
| 7,482,169 B2 | 1/2009 | Gjerde et al. | 436/178 |
| 7,534,623 B2 | 5/2009 | Landers et al. | 436/177 |
| 7,560,258 B2 | 7/2009 | Brueggemeier et al. | 435/174 |
| 7,608,234 B2 | 10/2009 | Stenzel et al. | 423/335 |
| 7,671,203 B2 | 3/2010 | Antonini | 546/44 |
| 7,674,835 B2 | 3/2010 | Rasmussen et al. | 521/31 |
| 7,683,011 B2 | 3/2010 | Putzig | 507/273 |
| 7,692,013 B2 | 4/2010 | Antonini | |
| 7,714,112 B2 | 5/2010 | Engstrand et al. | 530/390.6 |
| 7,732,383 B2 | 6/2010 | Putzig | 507/271 |
| 7,736,612 B2 | 6/2010 | Kubota | 423/335 |
| 7,745,582 B2 | 6/2010 | Lihme et al. | 530/387.1 |
| 7,754,660 B2 | 7/2010 | Putzig | 507/271 |
| RE41,595 E | 8/2010 | Shandle et al. | 210/635 |
| 7,780,946 B2 | 8/2010 | Wormsbecher | 423/659 |
| 7,790,657 B2 | 9/2010 | Putzig | 507/273 |
| 7,795,189 B2 | 9/2010 | Putzig | 507/273 |
| 7,795,190 B2 | 9/2010 | Putzig | 507/273 |
| 7,824,548 B2 | 11/2010 | DiLeo | 210/198.2 |
| 7,851,417 B2 | 12/2010 | Putzig | 507/271 |
| 7,875,317 B2 | 1/2011 | Nakagawa et al. | 427/387 |
| 7,897,051 B2 | 3/2011 | Sohling et al. | 210/670 |
| 7,919,177 B2 | 4/2011 | Jiang et al. | 428/304.4 |
| 7,922,908 B2 | 4/2011 | Allington et al. | 210/635 |
| 7,943,046 B2 | 5/2011 | Martosella et al. | 210/635 |
| 7,960,311 B2 | 6/2011 | Carlson | 506/13 |
| 7,994,092 B2 | 8/2011 | Gorkovenko et al. | 502/404 |
| 8,197,782 B2 | 6/2012 | DeVera | 423/339 |
| 8,242,050 B2 | 8/2012 | Lu et al. | 502/407 |
| 8,481,298 B2 | 7/2013 | Andersson et al. | 435/239 |
| 8,551,894 B2 | 10/2013 | Seshadri et al. | 442/63 |
| 8,658,277 B2 | 2/2014 | Wyndham et al. | |
| 8,673,988 B2 | 3/2014 | Graalfs et al. | 521/32 |
| 8,791,220 B2 | 7/2014 | Jiang et al. | |
| 9,556,258 B2 | 1/2017 | Nti-Gyabaah et al. | |
| 2002/0006493 A1 | 1/2002 | Chabrecek et al. | 428/64.1 |
| 2002/0012982 A1 | 1/2002 | Blakesley et al. | 435/183 |
| 2002/0028520 A1 | 3/2002 | Boschetti et al. | 438/518 |
| 2002/0043499 A1 | 4/2002 | Hammen et al. | 210/656 |
| 2002/0127587 A1 | 9/2002 | Simms et al. | 435/6 |
| 2002/0166816 A1 | 11/2002 | Allen et al. | 210/856 |
| 2003/0017464 A1 | 1/2003 | Pohl | 435/6 |
| 2003/0075508 A1 | 4/2003 | Woodruff et al. | 210/583 |
| 2003/0108879 A1 | 6/2003 | Klaerner et al. | 435/6 |
| 2003/0171443 A1 | 9/2003 | Erbacher | 521/27 |
| 2003/0187227 A1 | 10/2003 | Lihme et al. | 530/387.1 |
| 2003/0201229 A1 | 10/2003 | Siwak et al. | 210/850 |
| 2003/0225261 A1 | 12/2003 | Taylor et al. | 535/25.5 |
| 2004/0028901 A1 | 2/2004 | Rumpf et al. | 428/375 |
| 2004/0058059 A1 | 3/2004 | Linford | 427/58 |
| 2004/0091411 A1 | 5/2004 | Modrek-Najafabadi | 423/338 |
| 2004/0127648 A1 | 7/2004 | Guerrer et al. | 525/227 |
| 2004/0159611 A1 | 8/2004 | Urano | 210/856 |
| 2004/0203308 A1* | 10/2004 | Ko | A61F 13/15626 442/352 |
| 2004/0211724 A1 | 10/2004 | Gibson et al. | 210/638 |
| 2004/0224843 A1 | 11/2004 | Hammen et al. | 502/402 |
| 2004/0266896 A1 | 12/2004 | Britsch et al. | 521/38 |
| 2005/0029196 A1 | 2/2005 | Rhemrev-Boom | 210/658 |
| 2005/0032922 A1 | 2/2005 | Deorkar et al. | |
| 2005/0100905 A1 | 5/2005 | Nassoy et al. | 435/6 |
| 2005/0106602 A1 | 5/2005 | Akhavan-Tafti | 435/6 |
| 2005/0115903 A1 | 6/2005 | Hallier-Soulier et al. | 210/856 |
| 2005/0200025 A1 | 9/2005 | Casey et al. | 257/762 |
| 2005/0269257 A1 | 12/2005 | Voute et al. | 210/502.1 |
| 2005/0282294 A1 | 12/2005 | Britsch | 436/514 |
| 2006/0041035 A1 | 2/2006 | Poppe et al. | 523/200 |
| 2006/0058181 A1 | 3/2006 | Margetts | 502/159 |
| 2006/0105391 A1 | 5/2006 | Engel et al. | 435/7.1 |
| 2006/0120683 A1 | 6/2006 | Kamp et al. | 386/141 |
| 2006/0144770 A1 | 7/2006 | Granger et al. | 210/198.2 |
| 2006/0147344 A1 | 7/2006 | Ahn et al. | 422/70 |
| 2006/0180549 A1 | 8/2006 | Liu et al. | 210/556 |
| 2006/0240633 A1 | 10/2006 | Martosella et al. | 438/348 |
| 2007/0112178 A1 | 5/2007 | Johansson et al. | 530/387.1 |
| 2007/0135304 A1 | 6/2007 | Walter et al. | |
| 2007/0141325 A1 | 6/2007 | O'Gara et al. | 428/332 |
| 2007/0178465 A1 | 8/2007 | Sudor et al. | 435/6 |
| 2007/0181482 A1 | 8/2007 | Abudokirim et al. | 210/921.6 |
| 2007/0193954 A1 | 8/2007 | Busson | 210/656 |
| 2007/0215547 A1 | 9/2007 | O'Gara | 210/656 |
| 2007/0276131 A1 | 11/2007 | Ferre et al. | 530/420 |
| 2008/0017579 A1 | 1/2008 | Hermansson et al. | 210/658 |
| 2008/0025900 A1 | 1/2008 | Mori | 423/336 |
| 2008/0026486 A1 | 1/2008 | Cooper et al. | 436/518 |
| 2008/0033103 A1 | 2/2008 | Kameda et al. | 524/571 |
| 2008/0038750 A1 | 2/2008 | Piehler et al. | 435/7.1 |
| 2008/0053908 A1 | 3/2008 | Chordia et al. | 210/658 |
| 2008/0071003 A1 | 3/2008 | Sellergren et al. | |
| 2008/0116122 A1 | 5/2008 | Wheelwright et al. | 210/87 |
| 2008/0146454 A1 | 6/2008 | Cuppoletti et al. | 506/6 |
| 2008/0153100 A1 | 6/2008 | Rank et al. | 435/6 |
| 2008/0154029 A1 | 6/2008 | Balayan et al. | 538/25.4 |
| 2008/0164211 A1* | 7/2008 | Lindner | B01J 20/286 210/656 |
| 2008/0210615 A1 | 9/2008 | Joehnck et al. | 210/196.2 |
| 2008/0213906 A1 | 9/2008 | Aurand et al. | 436/83 |
| 2008/0223794 A1 | 9/2008 | Yamamichi et al. | 210/767 |
| 2008/0236824 A1 | 10/2008 | Putzig | 166/280.1 |
| 2008/0249326 A1 | 10/2008 | Nakajima et al. | 558/410 |
| 2008/0269368 A1 | 10/2008 | Wyndham et al. | 521/154 |
| 2008/0269475 A1 | 10/2008 | Sohling | 536/25.4 |
| 2008/0277346 A1 | 11/2008 | Kirkland et al. | 210/658 |
| 2008/0293959 A1 | 11/2008 | Liu et al. | 556/449 |
| 2008/0311681 A1 | 12/2008 | Johannsen et al. | 436/548 |
| 2009/0035876 A1 | 2/2009 | Williams et al. | 436/529 |
| 2009/0048439 A1 | 2/2009 | Weisburg et al. | 536/25.41 |
| 2009/0056541 A1 | 3/2009 | Davison et al. | 95/86 |
| 2009/0062519 A1 | 3/2009 | Okamoto et al. | 536/20 |
| 2009/0074709 A1 | 3/2009 | Koepsel et al. | 424/78.32 |
| 2009/0127501 A1 | 5/2009 | Kashima | 252/79.5 |

(56) References Cited

U.S. PATENT DOCUMENTS

| | | | |
|---|---|---|---|
| 2009/0151946 A1 | 6/2009 | Putzig | 166/280.2 |
| 2009/0151947 A1 | 6/2009 | Putzig | 166/280.2 |
| 2009/0170973 A1 | 7/2009 | Mattiasson et al. | 521/134 |
| 2009/0186093 A1 | 7/2009 | Liu et al. | 424/497 |
| 2009/0192342 A1 | 7/2009 | Coupard et al. | 685/533 |
| 2009/0197332 A1 | 8/2009 | Andreou et al. | 435/375 |
| 2009/0206034 A1 | 8/2009 | Nakajima | 210/636 |
| 2009/0211453 A1 | 8/2009 | Nassivera et al. | 96/153 |
| 2009/0221809 A1 | 9/2009 | Sohling et al. | 536/25.4 |
| 2009/0232950 A1 | 9/2009 | Brothers, Jr. et al. | |
| 2009/0246885 A1 | 10/2009 | Bian et al. | 436/601 |
| 2009/0277838 A1 | 11/2009 | Liu et al. | 210/656 |
| 2009/0294362 A1 | 12/2009 | Persson et al. | 210/656 |
| 2009/0297853 A1 | 12/2009 | Kirkland et al. | 428/403 |
| 2009/0306292 A1 | 12/2009 | Bendejacq et al. | 525/55 |
| 2009/0308599 A1 | 12/2009 | Dusterhoft et al. | 168/249 |
| 2009/0308811 A1 | 12/2009 | Tepper et al. | 210/656 |
| 2010/0022419 A1 | 1/2010 | Reed et al. | |
| 2010/0029794 A1 | 2/2010 | Yilmaz et al. | 521/63 |
| 2010/0055667 A1 | 3/2010 | Hage et al. | |
| 2010/0075404 A1 | 3/2010 | Templeton | |
| 2010/0099579 A1 | 4/2010 | Chilkoti et al. | 506/16 |
| 2010/0116743 A1 | 5/2010 | Pryor et al. | |
| 2010/0129830 A1 | 5/2010 | Deshayes et al. | 435/7.1 |
| 2010/0132251 A1 | 6/2010 | Sohling et al. | 44/388 |
| 2010/0156135 A1 | 6/2010 | Guckel et al. | 424/9.1 |
| 2010/0159254 A1 | 6/2010 | Oertli et al. | 428/447 |
| 2010/0181254 A1 | 7/2010 | Graalfs | 210/656 |
| 2010/0209723 A1* | 8/2010 | Tanaka | C08K 5/098 428/480 |
| 2010/0237019 A1 | 9/2010 | Aldegonda et al. | 210/670 |
| 2010/0255130 A1 | 10/2010 | Chen | 428/403 |
| 2010/0272996 A1 | 10/2010 | Holmes et al. | 426/402 |
| 2010/0310539 A1 | 12/2010 | Garcia-Bennett | |
| 2010/0310865 A1 | 12/2010 | Kumar et al. | 428/352 |
| 2011/0049042 A1 | 3/2011 | DiLeo et al. | 210/490 |
| 2011/0049056 A1* | 3/2011 | Wyndham | B01J 20/288 210/656 |
| 2011/0059845 A1 | 3/2011 | Fryxell et al. | |
| 2011/0065901 A1 | 3/2011 | Soice et al. | 530/368.1 |
| 2011/0100915 A1 | 5/2011 | Kanda et al. | 210/656 |
| 2011/0121229 A1 | 5/2011 | Linder et al. | 252/184 |
| 2011/0139717 A1 | 6/2011 | Malenfant et al. | 210/656 |
| 2011/0160104 A1 | 6/2011 | Wu et al. | 507/269 |
| 2011/0162153 A1 | 7/2011 | Niembro et al. | 8/142 |
| 2011/0186519 A1 | 8/2011 | Balayan et al. | 210/660 |
| 2011/0201078 A1 | 8/2011 | Rasmussen et al. | |
| 2011/0245077 A1 | 10/2011 | Anderson et al. | 502/402 |
| 2011/0284465 A1 | 11/2011 | Liu et al. | 210/656 |
| 2011/0313147 A1 | 12/2011 | Boschetti et al. | 536/56 |
| 2011/0313712 A1 | 12/2011 | Nikolyn et al. | 702/136 |
| 2012/0024791 A1 | 2/2012 | Deetz et al. | |
| 2012/0055860 A1 | 3/2012 | Wyndham | 210/198.3 |
| 2012/0065393 A1 | 3/2012 | Choi et al. | 540/456 |
| 2012/0071643 A1 | 3/2012 | Helfer et al. | 536/26.4 |
| 2012/0108803 A1 | 5/2012 | Han et al. | 536/24.5 |
| 2012/0205315 A1 | 8/2012 | Liu et al. | 210/656 |
| 2012/0231537 A1 | 9/2012 | Templeton | |
| 2012/0259094 A1 | 10/2012 | Hearn et al. | 530/367.7 |
| 2012/0283337 A1 | 11/2012 | Brick et al. | 514/772.4 |
| 2013/0020523 A1 | 1/2013 | Han et al. | |
| 2013/0041135 A1 | 2/2013 | Tamori et al. | 530/387.1 |
| 2013/0046056 A1 | 2/2013 | Spector et al. | 525/54.1 |
| 2013/0056415 A1 | 3/2013 | Kozlov et al. | 210/636 |
| 2013/0109072 A1 | 5/2013 | Tsunoda et al. | |
| 2013/0112623 A1 | 5/2013 | Fernandez-Lahore et al. | |
| 2013/0122215 A1 | 5/2013 | Waller et al. | |
| 2013/0131321 A1 | 5/2013 | Bittermann et al. | |
| 2013/0133516 A1 | 5/2013 | Okano et al. | 96/88 |
| 2013/0146542 A1* | 6/2013 | Huang | B01J 20/0262 210/656 |
| 2013/0178608 A1 | 7/2013 | Kulkarni et al. | |
| 2013/0189322 A1 | 7/2013 | Honeyman et al. | |
| 2013/0193052 A1 | 8/2013 | Witt et al. | |
| 2013/0245139 A1 | 9/2013 | Kozlov et al. | |
| 2013/0274451 A1 | 10/2013 | Bjorkman et al. | |
| 2013/0313187 A1 | 11/2013 | Yin et al. | 210/500.33 |
| 2014/0046023 A1 | 2/2014 | Gottschall et al. | B01J 20/286 |
| 2014/0046029 A1 | 2/2014 | Shannon et al. | C08F 271/02 |
| 2014/0093888 A1 | 4/2014 | Templeton | |

FOREIGN PATENT DOCUMENTS

| | | | |
|---|---|---|---|
| CN | 1898265 A | 1/2007 | |
| CN | 101553731 A | 10/2009 | |
| CN | 101381437 | 5/2011 | |
| CN | 102716727 A | 10/2012 | |
| CN | 102443120 | 3/2013 | C08F 292/00 |
| CN | 103289030 A | 9/2013 | |
| CN | 102675564 | 4/2014 | C08F 292/00 |
| CN | 103764662 A | 4/2014 | |
| DE | 102006012467 | 9/2007 | C08J 3/12 |
| EP | 0106769 | 1/1987 | |
| EP | 0263934 | 8/1987 | |
| EP | 0172579 | 11/1992 | B01J 20/32 |
| EP | 0545677 | 6/1993 | |
| EP | 0300273 | 3/1994 | |
| EP | 0520109 | 3/1995 | |
| EP | 0463036 | 9/1995 | |
| EP | 0490300 | 3/1998 | |
| EP | 0950067 | 10/1999 | |
| EP | 1229094 | 8/2002 | |
| EP | 1422521 A1 | 5/2004 | |
| EP | 1864999 | 12/2007 | |
| EP | 1897890 | 3/2008 | |
| EP | 1900751 | 3/2008 | |
| EP | 2217646 | 1/2013 | C08J 9/26 |
| EP | 2352771 | 1/2013 | C08F 220/58 |
| EP | 2616169 | 7/2013 | B01D 69/12 |
| EP | 1758671 | 9/2013 | B01D 63/10 |
| EP | 1690867 B1 | 10/2013 | |
| JP | 52-026386 A | 2/1977 | |
| JP | S5226386 A | 2/1977 | |
| JP | 59050052 | 3/1984 | |
| JP | 59050054 | 3/1984 | |
| JP | S59500656 A | 4/1984 | |
| JP | S60-114340 | 6/1985 | |
| JP | S62-235207 A | 10/1987 | |
| JP | S6486868 A | 3/1989 | |
| JP | H02142798 A | 5/1990 | |
| JP | H03-26961 A | 2/1991 | |
| JP | 06016738 | 1/1994 | |
| JP | 8134138 | 5/1996 | |
| JP | 2001521507 A | 11/2001 | |
| JP | 2003526796 A | 9/2003 | |
| JP | 2008012460 A | 1/2008 | |
| JP | 2009031277 A | 2/2009 | |
| JP | 2009126948 A | 6/2009 | |
| JP | 2011001336 | 1/2011 | |
| JP | 4683653 B2 | 5/2011 | |
| JP | 2011523624 A | 8/2011 | |
| JP | 2012012334 | 1/2012 | |
| JP | 2012032390 A | 2/2012 | |
| JP | 2012042477 A | 3/2012 | |
| JP | 2012086221 A | 5/2012 | |
| JP | 2012139678 A | 7/2012 | |
| JP | 2012254981 A | 12/2012 | |
| JP | 2013510918 | 3/2013 | C08J 9/35 |
| WO | 8303776 A1 | 11/1983 | |
| WO | 9400237 | 1/1994 | |
| WO | 9403268 | 2/1994 | |
| WO | 9525789 | 9/1995 | |
| WO | 9705174 | 2/1997 | |
| WO | 9831461 | 7/1998 | B01J 20/28 |
| WO | 0102452 | 1/2001 | |
| WO | 0188520 | 11/2001 | |
| WO | 0228912 | 4/2002 | |
| WO | 03031580 | 4/2003 | |
| WO | 03049671 | 6/2003 | |
| WO | 2004009677 | 1/2004 | |
| WO | 2004024318 | 3/2004 | |
| WO | WO-02/059591 A9 | 6/2004 | |
| WO | 2004076511 | 9/2004 | |
| WO | 2005005548 A1 | 1/2005 | |

(56) References Cited

FOREIGN PATENT DOCUMENTS

| WO | 2006110314 | 10/2006 | |
|---|---|---|---|
| WO | 2008027262 | 3/2008 | |
| WO | 2008140652 | 11/2008 | |
| WO | 2008147717 | 12/2008 | |
| WO | 2009053317 | 4/2009 | ............... C08F 2/44 |
| WO | 2009079325 | 6/2009 | |
| WO | 2009102207 | 8/2009 | |
| WO | 2009150402 | 12/2009 | |
| WO | 2010027955 | 3/2010 | ............ B01D 63/00 |
| WO | 2011012302 | 2/2011 | |
| WO | 2011025867 | 3/2011 | ............ B01D 61/00 |
| WO | 2012087231 | 6/2012 | |
| WO | 2013004587 | 1/2013 | ............... C07K 1/18 |
| WO | 2013007793 | 1/2013 | ............ B01J 20/283 |
| WO | 2013062105 | 5/2013 | |
| WO | 2013089477 | 6/2013 | ............ C07K 16/28 |
| WO | 2013162449 A1 | 10/2013 | |
| WO | 2014043644 A1 | 3/2014 | |
| WO | 2014058570 A1 | 4/2014 | |

OTHER PUBLICATIONS

Capito, Florian; Bauer, Johann; Rapp, Almut; Schröter, Christian; Kolmar, Harald; Stanislawski, Bernd, "Feasibility Study of Semi-Selective Protein Precipitation with Salt-Tolerant Copolymers for Industrial Purification of Therapeutic Antibodies", Biotechnology and Bioengineering, v 110, n 11, p. 2915-2927 (2013).

Carrot, Geraldine; Perez, Henri, "Controlled Surface Initiated Polymerizations from Inorganic Nanoparticles", Polymer Preprints (American Chemical Society, Division of Polymer Chemistry), 47(2), 827-828 (2006).

Chen, Xin; Tolley, H. Dennis; Lee, Milton L., "Polymeric Cation-Exchange Monolithic Columns Containing Phosphoric Acid Functional Groups for Capillary Liquid Chromatography of Peptides and Proteins", Journal of Chromatography A, v 1217, n 24, p. 3844-3854 (2010).

Dhar, P.; Vatansever, F.; Seery, "Modification of Silica Surfaces Using Surface Initiated Polymerization", Book of Abstracts, 215th ACS National Meeting, Dallas, Mar. 29-Apr. 2, PMSE-147 (1998).

Dyer, Daniel J.; Zhao, Tongfeng; Green, John-Bruce, "Surface Initiated Photopolymerization from Gold", Polymer Preprints (American Chemical Society, Division of Polymer Chemistry), 42(2) (2001).

Binghe Gu, Yun Li and Lee, Milton L., "Polymer Monoliths with Low Hydrophobicity for Strong Cation-Exchange Capillary Liquid Chromatography of Peptides and Proteins", Analytical Chemistry, v 79, n 15, p. 5848-5855 (2007).

Guo, Hui, "Development of Chromatofocusing Techniques Employing Mixed-Mode Column Packings for Biomolecule Separations", Dissertations & Theses, University of Maryland, Baltimore County, ProQuest, UMI Dissertations Publishing (2014).

Huang, Meiyu; Wu, Ru, "Polymerization of Acrylic Acid Initiated by Poly(y-mercaptopropylsiloxane-lanthanide) Complexes", Ziran Zazhi, 5(12), 950-1 (1982).

Kuroda, Hirofumi; Nakatsuchi, Sayaka; Kitao, Nobuyoshi; Nakagawa, Tsuyoshi; "Radical polymerization of Methacrylates Having Moiety Activated by Electron-Withdrawing Group as a Reactive Functional Group" Relative & Functional Polymers, v 66, p. 229-238 (2006).

Liu, Shu-juan; Zhou, Feng; Jiang, Sheng-xiang; Liu, Wei-min, "Characterization of Polymer Brushes on Nanoparticle Surfaces" Gaofenzi Cailiao Kexue Yu Gongcheng, 19(6), 65-68 (2003).

Liu, Shu-juan; Dun, Hui-juan; Zhou, Feng; Zhao, Liang; Liu, Xia; Jiang, Sheng-xiang, "Preparation of Polymer Modified Stationary Phases through Surface Radical Chain Transfer Reaction" Sepu, 20(5), 432-435 (2002).

Liu, Shu-juan; Zhou, Feng; Jiang, Sheng-xiang; Liu, Wei-min, "Preparation of Stationary Phase for HPLC Through Surface-Initiated Polymerization" Gaofenzi Cailiao Kexue Yu Gongcheng, 19(6), 65-68 (2003).

Mihai, M.; Schwarz, S.; Janke, A.; Ghiorghia, C.A.; Dragan, E.S., "Silica Microparticles Surface Coating by Layer-by-Layer or Polyelectrolyte Complex Adsorption", Periodical: Journal of Polymer Research, v 20, n 2, 89 (2013).

Min, Jun Ho; Min, Seong Kee, "The Characteristics of Poly(acrylamide)-SiOx Nanoparticles Prepared by Graft-Polymerization", Periodical: Kongop Hwahak, 21(1), 34-39 (2010).

Murofushi, Katsumi, "Additive for Increase in Hardness and Adhesiveness of Photocurable Resin", Periodical: Purasuchikkusu, 57(9), 37-40 (2006).

Park, Mi-kyoung; Sakellariou, George; Pispas, Stergios; Hadjichristides, Nikos; Mays, Jimmy; Advincula, Rigoberto, "Living Anionic Surface Initiated Polymerization (LASIP): Synthesis and Characterization of Block Copolymers", Periodical: Abstracts of Papers, 223rd ACS National Meeting, Orlando, FL, United States, Apr. 7-11, 2002.

Prucker, Oswald; Habicht, Jorg; Park, In-Jun; Ruhe, Jurgen, "Photochemical Strategies for the Preparation, Micropatterning and Modification of Polymer Brushes", Periodical: Polymer Preprints (American Chemical Society, Division of Polymer Chemistry), 44(1), 470-471 (2003).

Salarizadeh, Parisa; Javanbakht, Mehran; Abdollahi, Mahdi; Naji, Leila, "Preparation, Characterization and Properties of Proton Exchange Nanocomposite Membranes Based On Poly(Vinyl Alcohol) and Poly(Sulfonic Acid)-Grafted Silica Nanoparticles" International Journal of Hydrogen Energy, v 38, n 13 (2013).

Shimomura, Masato; Kikuchi, Hiroaki; Matsumoto, Hiroshi; Yamauchi, Takeshi; Miyauchi, Shinnosuke "Attaching pf Poly(acrylic acid) to Inorganic Surface and its Application to Enzyme Immobilization" Polymer Journal, v 27, n 9, p. 974-977 (1995).

Srivastava, Arti; Behari, Kunj, "Graft Copolymerization of 2-Acrylamido-2-Methyl-1-Propane Sulphonic Acid onto Xanthan Gum by Ascorbic / Bromate Redox Pair" PMSE Preprints, 90, 698-699 (2004).

Wang, Xiao-hua; Gao, Bao-jiao; Wang, Ming-juan; Fang, Xiao-lin, "Realizing Highly Effective Graft-Polymerization of Acrylonitrile on Surfaces of Silica Gel Particles by Constructing Mercapto Group-Cerium (IV) Salt Redox Initiation System" Gaofenzi Xuebao, (3), 256-263 (2012).

Zhang, Wenjun; Hu, Baoan; Zhang, Yan; Su, Hui; Xiao, Min, "Preparation of Novel Amphiphilic Polymeric Flocculant by Dispersion Polymerization Method", Huaxue Gongcheng, 37(2), 67-70 (2009).

Shukla, J.S.; Singh, Khajan "Aqueous Polymerization of Acrylamide", Journal of Polymer Science: Polymer Chemistry Edition, vol. 17, 531-538 (1979).

Rashid, Harun-Or; Lee, Won-Ki; Hong, Seong-Soo; Park, Jong Myung; Kim, Hyun Gyu; Lim, Kwon Taek "Polymer Brushes on Carbon Nanotubes by Thiol-Lactam Initiated Radical Polymerization of 2-Hydroxyethyl Methacrylate", Journal of Nanoscience and Nanotechnology, v 12, p. 840-846 (2012).

Okaya, Takuji; Kikuchi, Kenji; Morii, Yukiko "Polymerization of Acrylamide in Aqueous Medium Initiated with a Redox System Composed of Cysteine and Potassium Bromate" Macromolecular Chemistry and Physics, v 198, p. 2027-2034 (1997).

Maiti, Sukumar; Palit, Santi "Thiols as Redox Initiator for Vinyl Polymerization" Journal of Polymer Science: Polymer Chemistry, v 9, n 1, p. 253-256 (1971).

PCT Search Report and Written Opinion for PCT/US2015/28476; dated Jul. 27, 2015.

European Search Report for 15785536.2; dated Nov. 20, 2017.

Boyle, M.D.P.; Reis, K.J. "Bacterial Fc Receptors", Nature Biotechnology 5, p. 697-703 (1987).

Brunauer, Stephen, Emmett, P.H., Teller, Edward "Adsorption of Gases in Multimolecular Layers" Journal of American Chemical Soceity, 60, p. 309-319 (1938).

Bruno, G.; Gasparrini, F.; Misiti, D.; Arrigoni-Martelll. E.; Bronzetti, M. "High-performance liquid chromatographic separation of biomolecules using calcium phosphate supported on macroporous silica microparticles", Journal of Chromatography, v 504, n 2, p. 319-333, 19g0; ISSN: 00219673, Publisher: Elsevier.

(56) References Cited

OTHER PUBLICATIONS

Buess-Herman, Claudine et al. "Hydration of a Polysulfone Anion-Exchange Membrane Studied by Vibrational Spectroscopy," Langmuir, vol. 19, No. 8 (2003).
Emara, Samy; Masujima, Tsutomu; Hadad, Ghada: Kamal, Maha; Zaazaa, Hala; Kawi, Mohamed Abdel, "A Rapid, Sensitive, and Environmentally Friendly On-Line Solid Phase Extraction Using Protein-Coated IJ-Bondapak Cyanide Silica Precolumn for Chromatographic Determination of Paracetamol in Human Serum.", Journal of Liquid Chromatography and Related Technologies, v 36, n 10, p. 1297-1311, Apr. 1, 2013; ISSN: 10826076, E-ISSN: 1520572X; DOI: 10,1080/10826076.2012,686139; Publisher: Taylor and Francis Inc.
Hatch, R.G., "Chromatography of Proteins On a Silica-Based Support with Polyethylene No Glycol ligands", Journal of Chromatographic Science, v 28, n 4, p. 210-214, Apr. 1990; ISSN: 00219665.
Hernstrom, Petrus et al. "Atom-Transfer Radical Graft Polymerization Initiated Directly from Silica Applied to Functionalization of Stationary Phases for High-Performance Liquid Chromatography in the Hydrophilic Interaction Chromatography Mode," Analytical Chemistry, 78 (2006), pp. 7098-7103.
Jandera, Pavel, "Stationary phases for hydrophilic interaction chromatography, their characterization and implementation into multi-dimensional chromatography concepts." Journal of Separation Science, v 31, n 9, pp. 1421-1437, May 2008, Hydrophilic interaction chromatography; ISSN: 16159306, E-ISSN: 16159314; DOI: 10.1002/jssc.200800051, Publisher: Wiley-VCH Verlag.
Katoh, Shigeo et al. "Affinity Purification of Antibodies: Optimization Strategies of Protein A-Coupled Silica Media", G.I.T. Laboratory Journal May-Jun. 2007 p. 26-27.
Katoh, Shigeo, "Affinity chromatography for large-scale purification of antibody pharmaceuticals", Biotechnology-based drug manufacturing technology series. Pharm Tech Japan, v 27, No. 11, 2011.
Katoh, Shigeo; Imada, Masami; Takeda, Naoki; Katsuda, Tomohlsa; Miyahara, Hiroyoshi; Inoue, Masaki; Nakamura, Shuji, "Optimization of silica-based media for antibody purification by protein A affinity chromatography", Journal of Chromatography A, v 1161, n 1-2, p. 36-40, Aug. 17, 2007, 26th International Symposium on the Separation of Proteins, Peptides and Polynucleotfdes; ISSN: 00219673; DOI: 10.1016/j.chroma.2007,04.023; Publisher: Elsevier.
Ma, Z et al. "Synthesis of Magnetic Chelator for High-Capacity Immobilized Metal Affinity Adsorption of Protein by Cerium Initiated Graft Polymerization." Langmuir, vol. 21, No. 15 (2005).
Manda, Keerthini "Synthesis and characterization of protein bonded stationary phases for HPAC.", Source: Dissertations & Theses, 2007. vol. 46, Issue 1, Publication I order No. AAI1445247; http://search.proquest.com/docviewf33934537?accountid=142944.
Massom, L R; Ulbright, C; Snodgrass, P; Jarrett, H W, "Protein A-silica: Purification of Antibodies and Antigen/Antibody Complexes by High Pressure Affinity Chromatography", Biochromatography 4.3 (1989): 144-148; http://search. proquest.com/docview/15419101?accountid=142944.
McCue, Justin T.; Kemp, Glen; Low, Duncan; Quiniones-Garcia, Igor, "Evaluation of protein-A chromatography media", Science Direct_Journal of Chromatography A, 989 (2003) 139-153.
Miyahara, H; Nakashima, R; Inoue, M; Katsuda, T; Yamaji, H. Katoh, S; "Optimization and Performance of Silica-Based Media for Industrial-Scale Antibody Purification" Chemical Engineering & Technology (2012), 35, No. 1, 157-160. Publisher. Wiley-VCH Verlag.
Moon, Jung-Min et al. "Modification of Monodisperse Colloidal Silica by Radical Copolymerization of Cationic Surface Active Vinyl Monomers," Polymer Journal, vol. 41, No. 3 (2009), pp. 208-213.
Mori, Hideharu et al. "Controlled Radical Polymerization of an Acrylamide Containing I-Phenylalanine Moiety via RAFT." Macromolecules, No. 38, p. 9055-9065 (2005).
Narayanan, S.; CraneS., "Affinity Chromatography Supports: A Look at Performance Requirements", Trends in Biotechnology, vol. 8, 1990, pp. 12-16; DOI: 10.1016/0167-7799(90)90124-G; Publisher: Elsevier.
Ohlson S, Wieslander J, "High-Performance Liquid Affinity Chromatographic Separation of Mouse Monoclonal Antibodies with Protein A Silica.", J Chromatogr. Jun. 26, 1987;397:207-12; Publisher: Elsevier.
Roy, Asit; Roy, Sujata, "Preparation of a high flow packing material (silica based) for high performance affinity chromatography of proteins." Affinity Chromatography and Biological Recognition, 1983, AMF Speciality Materials Group Meriden, Connecticut, USA, ISBN 0-12-166580-1. Publisher: Academic Press, Inc.
Savina, Irina et al. "Anion-Exchange Supermacroporous Monolithic Matrices with Grafted Polymer Brushes of N,N-Dirnethylaminoethyi-Methacrylate," Journal of Chromatography A, vol. 1092, No. 2 (2005).
Savina, Irina et al. "ion-Exchange Macroporous Hydrophilic Gel Monolith with Grafted Polymer Brushes." J. Mol. Recognit., vol. 19, No. 4 (2006).
Schmidt, D.E.; Giese, R.W.; Conran, D.; Karger, B.L, "High performance liquid chromatography of proteins on a dial-bonded silica gel stationary phase", Analytical Chemistry, v 52, n 1, 177-82, Jan. 1980; ISSN: 0003-2700; Country of publication: USA. Publisher. American Chemical Society.
Tessrkmen, Deniz et al. "Synthesis of Tentacle-Type Magnetic Beads as Immobilized Metal-Chelate Affinity Support for Cytochrome C Adsorption," Int. J. Bioi. Macromol., vol. 38, No. 2 (2006).
Tsuneda, Setal. "Biding of Lysozyme onto a Cation-Exchange Microporous Membrane Containing Tentacle-Type Grafted Polymer Branches," Biotechnol Prog., vol. 10, No. 1 (1994).
Vuignier, Kanne; Fekete, Szabolcs; Carrupt, Pierre-Aiain; Veuthey, Jean-Luc; Guillarme, Davy, "Comparison of Various Silica-Based Monoliths for the Analysis of Large Biomolecules", Journal of Separation Science, v 36, n 14, p. 2231-2243, Jul. 2013; ISSN: 16159306, E-ISSN: 16159314; DOI: 10.1002/jssc.201300323; Publisher: Wiley.VCH Verlag.
Wei, Bingchuan, "Silica colloidal crystals for ultra-efficient protein separations", Dissertations & Theses, Purdue University, ProQuest, UMI Dissertations Publishing, 2011. 3506193; ISBN 9781267315243; http://search.proquest.com/docview/1014174524?accountid=142944, Publisher. UMI Dissertations Publishing 2011.
Xu, Liang et al. "Fabrication and Characterization of Open-Tubular CEC Modified with Tentacle-Type Metal Chelating Polymer Chains," Electrophoresis, vol. 28, No. 11 (2007).
Xu, Liang et al. "Novel Negatively Charged Tentacle-Type Polymer Coating for On-Line Preconcentration of Proteins in CE." Electrophoresis, vol. 30, No. 4 (2009).
Xu, Liang et al. "Novel Open Tubular CEC with Tentacle-Type Polymer Stationary Phase Functionalized by Phenylalanine." Electrophoresis, vol. 29, No. 4 (2008).
Yanase, Tomohiro et al. "Regeneration Technology of Tetramethylammonium Hydroxide Using ton Exchange Resin." Technology Reports of Kansai University, No. 47 (2005).
Yoshinaga, Kohji; Kondo, Akihiko; Higashitani, Ko; Kito, Taketoshi, "Immobilization of Protein On Monodispersed Colloidal Silica with Poly(Ethylene Glycol) Spacer and Application of the Composites to Immunological Agglutination Tests", Colloids and Surfaces A: Physicochemical and Engineering Aspects, v 77, n 2, p. 101-107, Sep. 17, 1993; ISSN: 09277757; DOI: 10.1 016/0927-7757(93)80106-0.
Zhang, Jian et al. "Capillary Electrochromatography of Peptides on a Column Packed with Tentacular Weak Cation-Exchanger Particles," Journal of Chromatography A, 953 (2002), pp. 239-249.
Terada K., et al., Syntheses and Properties of Block Copolymers Having Poly (vinyl alcohol) as One Component, Japanese Journal of Polymer Science and Technology, Japan, Nov. 1992, Vol.49, No. 11, p. 885-891.
Koizumi K., Separation and Analysis of Carbohydrates, Journal of Applied Glycoscience, 1994, vol. 41, No. 4, p. 465-471.
Ihara H., Functional Design of Polymer-coated Silica and Its High Selectivity, Abstracts from the 14th Symposium on Adsorption, Japan, Aug. 2003, p. 1-7.

(56) References Cited

OTHER PUBLICATIONS

Patent Application No. JP 2016-565107 Office Action dated Nov. 1, 2019.
Patent Application No. JP 2017-510439 Office Action dated Mar. 5, 2020.
Patent Application No. 201580036306.5 English translation of First Office Action and Search Report dated Jan. 19, 2020.
Feng et al., "Silica-based strong anion exchange media for protein purification", Journal of Chromatography A, Dec. 8, 2014, pp. 53-63, 1376 (2015).
Decision on Rejection on CN Application No. 201580036306.5 dated Oct. 19, 2021 (30 pages, English translation included).
European Communication pursuant to Article 94(3) EPC on EP Application No. 15785536.2 dated Apr. 5, 2019 (6 pages).
European Communication pursuant to Article 94(3) EPC on EP Application No. 15785536.2 dated Nov. 11, 2019 (5 pages).
European Summons to attend oral proceedings pursuant to Rule 115(1) EPC on EP Application No. 15785536.2 dated Oct. 1, 2021 (7 pages).
First Examination Report on IN Application No. 201617037359 dated Oct. 11, 2019 (8 pages, English translation included).
Hearing Notice on IN Application No. 201617037359 dated May 10, 2021 (2 pages, English translation included).
Horak, J., et al., "Contribution of sulfonyl-aromatic and sulfonic acid-aromatic interactions in novel sulfonyl/sulfonic acid-embedded reversed phase materials," Journal of Chromatography, 1191(1-2):141-156(2007).
International Preliminary Report on Patentability on PCT/US2015/028476 dated Nov. 8, 2016 (6 pages).
Notice of Reasons for Refusal on JP Application No. 2017-510439 dated Feb. 16, 2021 (6 pages, English translation included).
Notice of Reasons for Refusal on JP Application No. 2017-510439 dated Mar. 14, 2019 (10 pages, English translation included).
Second Office Action on CN Application No. 201580036306.5 dated Dec. 4, 2020 (27 pages, English translation included).
Third Office Action on CN Application No. 201580036306.5 dated May 10, 2021 (22 pages, English translation included).
Yang, H., "Preparation of organic-silica hybrid monolithic col. and its application in capillary electrochromatography," Chinese Master's Theses Full-Text Databases: Engineering Technology, 1(4):38-48 (2014) (English abstract included).
Yang, H., et al., "One-pot synthesis of (3-sulfopropyl methacrylate potassium)-silica hybrid monolith via thiol-ene click chemistry for CEC," Electrophoresis, 34(4):510-517 (2013).

* cited by examiner

FUNCTIONALIZED SUPPORT MATERIAL AND METHODS OF MAKING AND USING FUNCTIONALIZED SUPPORT MATERIAL

FIELD OF THE INVENTION

The present invention relates generally to functionalized support material suitable for use in chromatography columns or cartridges. The present invention further relates to chromatography columns or cartridges containing the functionalized support material, methods of making functionalized support material, and methods of using functionalized support material, for example, as separation media in a chromatography column or cartridge.

BACKGROUND OF THE INVENTION

Cation and anionic exchange chromatographic materials are known. Cation exchange chromatographic materials typically contain media having surface attached anionic groups such as sulfonic acid groups (e.g., S strong cation exchanger) and/or carboxylic acid groups (e.g., CM weak cation exchanger). Anion exchange chromatographic materials typically contain media having surface attached cationic groups such as quaternary ammonium (e.g., Q strong anion exchanger) and/or diethylaminoethyl (e.g., DEAE weak anion exchanger).

In separation processes, such as protein purification, given the extremely high molecular weight (MW) and the slow moving of biomolecules, diffusion of the high MW biomolecules to the media surface is very slow and limited. To address this problem, the "tentacle" concept was developed and found to be very useful and widely applied. In the "tentacle" concept, tentacles comprising grafted polymer chains are grafted onto the surface of the media. The grafted polymer chains contain repeating units of ionic groups, connected from the end of the polymers to the surface of the media. These polymer chains can rotate freely, allowing interactions between protein molecules and polymeric stationary phase without requirements of the biomolecules to diffuse onto the surface of the media and thus enable high protein loading.

The most common chemistry involved in the tentacle coating concept utilizes the "graft from" concept. In such chemistries, radical polymerization is initiated from the surface of the media particles. For cation exchange media, Ce(IV) salt (e.g., U.S. Pat. No. 5,453,186 to E. Merck) is utilized to allow redox chemistry to surface diol groups (e.g., prepared through hydrolysis of attached epoxy groups prior to polymerization) to generate surface radicals, which polymerize sulfonic acid-containing monomers such as 2-acrylamido-2-methyl-1-propanesulfonic acid (AMPS). This chemistry is very costly in terms of both raw materials (monomer, Ce salt) and processes (e.g., process control, waste generation during cleanup and disposal, etc.).

Other ways of growing polymers, including some newly developed living polymerization techniques, have been developed during the past 20 to 25 years. Such techniques include, for example, Atom Transfer Radical Polymerization (ATRP) or Reversible Addition-Fragmentation chain Transfer (RAFr), etc. However, such technologies are of high cost, and have not been realized commercially in large scale production.

Efforts continue to develop cost-effective media suitable for use as cation and/or anionic exchange chromatographic materials, as well as cost-effective methods of making such media.

SUMMARY OF THE INVENTION

The present invention is directed to cost-effective media suitable for use, for example, as cation and/or anionic exchange chromatographic materials. The disclosed media, referred to herein as "functionalized support material," "functionalized particulate support material," and/or "chromatographic material," is suitable for use, for example, in chromatography columns or cartridges, such as in a high pressure liquid chromatography (HPLC) column or a fast protein liquid chromatography (FPLC) column. The present invention is also directed to methods of making functionalized support material, such as functionalized particulate support material.

The present invention is directed to functionalized support material. In one exemplary embodiment, the present invention is directed to functionalized support material comprising support material; and polymer chains extending from a surface of the support material, the polymer chains being covalently bonded to the surface via a divalent sulfur bond —S—, wherein (1) the polymer chains comprise (i) one or more positive charges thereon, (ii) one or more negative charges thereon, (iii) one or more ionizable functional groups that can form a positive or negative charge via dissociation or association of an atom (e.g., hydrogen) or an ion (e.g., proton), or (iv) any combination of (i) to (iii); or (2) the polymer chains are also covalently bonded to the surface thru (i) a second divalent sulfur bond —S—, (ii) a divalent oxygen bond —O— and a divalent silicon bond —Si— with the divalent oxygen bond —O— being positioned between the divalent silicon bond —Si— and the polymer chain, or (iii) both (i) and (ii); or (3) the support material further comprises at least one bifunctional second compound extending from the surface of the support material, each of the at least one bifunctional second compound comprising (i) one or more functional groups capable of bonding the bifunctional compound to the surface, and (ii) one or more hydrophilic groups; or (4) any combination of (1) to (3).

In another exemplary embodiment, the present invention is directed to a method of making functionalized support material. In one exemplary embodiment, the method of making functionalized support material comprises reacting support material with one or more first reactants so as to form an intermediate product having thiol groups thereon; and polymerizing one or more monomers onto the intermediate product via the thiol groups so as to form polymer chains covalently bonded to the thiol groups, wherein (1) the polymer chains comprise (i) one or more positive charges thereon, (ii) one or more negative charges thereon, (iii) one or more ionizable functional groups that can form a positive or negative charge via dissociation of an atom (e.g., hydrogen), or (iv) any combination of (i) to (iii); or (2) the polymer chains are also covalently bonded to the particle surface thru (i) a second divalent sulfur bond —S—, (ii) a divalent oxygen bond —O— and a divalent silicon bond —Si— with the divalent oxygen bond —O— being positioned between the divalent silicon bond —Si— and the polymer chain, or (iii) both (i) and (ii); or (3) the support material further comprises at least one bifunctional second compound extending from a surface of the support material, each of the at least one bifunctional second compound comprising (i) one or more functional groups capable of bonding the bifunctional compound to the surface, and (ii) one or more hydrophilic groups; or (4) any combination of (1) to (3).

The invention is further directed to a method of making a chromatographic material. In one embodiment, the method comprises reacting support material with one or more first reactants so as to form an intermediate product having thiol groups thereon; and polymerizing one or more monomers onto the intermediate product via the thiol groups so as to form polymer chains covalently bonded to the thiol groups, wherein the polymer chains comprise (i) one or more positive charges thereon, (ii) one or more negative charges thereon, (iii) one or more ionizable functional groups that can form a positive or negative charge via dissociation or association of an atom (e.g., hydrogen) or an ion (e.g., proton), or (iv) any combination of (i) to (iii).

The disclosed methods of making functionalized support material and/or chromatographic material may comprise a polymerizing step utilizing a reaction mixture free of organic solvent. In some embodiments, the polymerizing step utilizes a reaction mixture comprising (i) the intermediate product having thiol groups thereon, (ii) the one or more monomers, (iii) one or more oxidizing agents or a radical initiator, (iv) deionized water, and optionally (v) one or more organic solvents. In other embodiments, the polymerizing step utilizes a reaction mixture comprising (or consisting essentially of, or consisting of) (i) the intermediate product having thiol groups thereon, (ii) the one or more monomers, (iii) one or more oxidizing agents or a radical initiator, (iv) deionized water, and (v) one or more organic solvents.

In some exemplary embodiments, the methods of making functionalized support material or chromatographic material comprise reacting support material with one or more first reactants so as to form an intermediate product having thiol groups thereon; and polymerizing one or more monomers onto the intermediate product via the thiol groups so as to form polymer chains covalently bonded to the thiol groups, the polymerizing step utilizing a reaction mixture comprising (i) the intermediate product having thiol groups thereon, (ii) the one or more monomers, (iii) one or more oxidizing agents or a radical initiator, (iv) deionized water, and (v) optionally one or more organic solvents; wherein the one or more first reactants comprise (1) at least one bifunctional linking compound comprising (i) one or more functional groups capable of bonding the linking compound to the support material, (ii) one or more additional functional groups capable of covalently bonding with a compound comprising one or more thiol groups, and (iii) one or more atoms selected from the group consisting of C, O, Si and S, and (2) at least one bifunctional thiol-containing compound comprising (i) one or more functional groups capable of covalently bonding with the one or more additional functional groups of the linking compound, and (ii) one or more thiol groups. In some embodiments, the one or more first reactants comprise (i) at least one epoxy silane such as (3-glycidoxypropyl)-trimethoxysilane, (ii) 1,2-ethanedithiol, or (iii) a combination of (3-glycidoxypropyl)-trimethoxysilane and 1,2-ethanedithiol.

In the disclosed methods of making functionalized support material and/or chromatographic material, desirably, polymer chains formed on the support material are covalently bonded directly to thiol groups extending from the support material surface. In other words, in desired embodiments, a first monomeric unit of a given polymer chain is covalently bonded directly to the sulfur atom of a given thiol group.

In one desired embodiment, the present invention is directed to functionalized support material in the form of chromatographic material comprising support material; and polymer chains extending from a surface of the support material, the polymer chains being covalently bonded to the surface via a divalent sulfur bond —S—, wherein the polymer chains comprise (i) one or more positive charges thereon, (ii) one or more negative charges thereon, (iii) one or more ionizable functional groups that can form a positive or negative charge via dissociation or association of an atom (e.g., hydrogen) or an ion (e.g., proton), or (iv) any combination of (i) to (iii). Desirably, the polymer chains are covalently bonded directly to the sulfur atom of the divalent sulfur bond —S— (i.e., there are no other atoms between the sulfur atom and the first monomeric unit of the polymer chain). The chromatographic material may further comprise (1) polymer chains covalently bonded to the surface thru (i) a second divalent sulfur bond —S—, (ii) a divalent oxygen bond —O— and a divalent silicon bond —Si— with the divalent oxygen bond —O— being positioned between the divalent silicon bond —Si— and the polymer chain, or (iii) both (i) and (ii); or (2) at least one bifunctional second compound extending from the surface of the support material, each of the at least one bifunctional second compound comprising (i) one or more functional groups capable of bonding the bifunctional compound to the surface, and (ii) one or more hydrophilic groups; or (3) both (1) and (2).

The present invention is further directed to methods of using functionalized support material, columns or cartridges in combination with functionalized support material, and apparatus to detect the presence of one or more analytes (e.g., one or more biomolecules) in a given sample. In one exemplary embodiment, the present invention is directed to a method of using functionalized support material or chromatographic material, wherein the method comprises a method of analyzing a test sample comprising analyzing a test sample that potentially contain at least one analyte (e.g., a biological compound such as a protein or peptide), wherein the method comprises bringing the sample containing at least one analyte (e.g., a biological compound such as a protein or peptide) into contact with the herein-disclosed functionalized support material or chromatographic material of the present invention. For example, the disclosed methods of analyzing test samples may be used to detect the presence of at least one biological compound comprising a protein, a peptide, a polypeptide, a non-peptidyl compound, a polyene macrolide, a terpene, an alkaloid, a carbohydrate, an oligonucleotide, a derivative thereof, an analogue thereof, or any combination thereof.

In other desired embodiments, the support material used in the above-described methods and functionalized materials comprises particulate material. In some embodiments, the support material comprises inorganic particles such as silica particles. In other embodiments, the support material comprises polymeric particles such as polymethylmethacrylate resin particles. In other embodiments, the support material comprises non-particulate support materials such as chromatography membranes made with stabilized reinforced cellulose.

These and other features and advantages of the present invention will become apparent after a review of the following detailed description of the disclosed embodiments and the appended claims.

BRIEF DESCRIPTION OF THE FIGURES

The present invention is further described with reference to the appended figures, wherein.

DETAILED DESCRIPTION OF THE INVENTION

Figure 1:
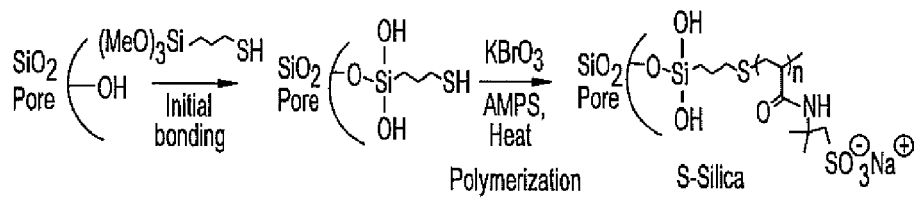
FIG. 1 provides an exemplary reaction scheme for preparing functionalized support material or chromatographic material of the present invention.

It should be understood that although the herein-described methods and functionalized support material are described as "comprising" one or more features, steps or components, the above-described methods and functionalized support material may "comprise," "consists of," or "consist essentially of" any of the above-described features and/or steps and/or components of the methods and functionalized support material. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited features, steps or components. For example, a method or functionalized support material that "comprises" a list of elements (e.g., components or features or steps) is not necessarily limited to only those elements (or components or features or steps), but may include other elements (or components or features or steps) not expressly listed or inherent to the method and/or functionalized support material.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define methods and functionalized support material that include materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described methods and/or functionalized support material may comprise, consist essentially of, or consist of any of the herein-described steps, components and features, as shown in the figures with or without any additional feature(s) not shown in the figures. In other words, for example, in some embodiments, the methods and/or functionalized support material of the present invention may have any additional feature, step and/or component that is not specifically shown in the figures. In some embodiments, the methods and/or functionalized support material of the present invention do not have any additional features, steps and/or components other than those (i.e., some or all) shown in the figures, and such additional features, not shown in the figures, are specifically excluded from the methods and/or functionalized support material.

I. Functionalized Support Material

Functionalized support material of the present invention comprises a support material; and polymer chains extending from a surface of the support material, the polymer chains being covalently bonded to the surface thru a divalent sulfur bond —S—, wherein (1) the polymer chains comprise (i) one or more positive charges thereon, (ii) one or more negative charges thereon, (iii) one or more ionizable functional groups that can form a positive or negative charge via dissociation or association of an atom (e.g., hydrogen) or an ion (e.g., proton), or (iv) any combination of (i) to (iii). In some embodiments, (2) the polymer chains are also covalently bonded to the support material surface thru (i) a second divalent sulfur bond —S—, (ii) a divalent oxygen bond —O— and a divalent silicon bond —Si— with the divalent oxygen bond —O— being positioned between the divalent silicon bond —Si— and the polymer chain, or (iii) both (i) and (ii); or (3) the support material further comprises at least one bifunctional second compound extending from the surface of the support material, each of the at least one bifunctional compound comprising (i) one or more functional groups capable of bonding the bifunctional compound to the surface, and (ii) one or more hydrophilic groups; or (4) any combination of (1) to (3).

Support material useful in the present invention comprises various materials, including but not limited to organic materials, inorganic materials, hybrid organic/inorganic materials and combinations thereof. Suitable inorganic materials for use as support material in the present invention include products commercially available as chromatographic media. The inorganic supports may be prepared using methods known in the art. The inorganic particles provide support for one or more additional components applied to a surface of the inorganic particle. In an embodiment of the invention, the inorganic oxide material include, but is not limited to, inorganic oxides, silicates, alumina silicates, glass e.g. controlled pore glass or CPG, ceramics, graphite and combinations thereof. An inorganic metal oxide is more desirable. Inorganic oxides suitable for use as support material in the present invention typically have free hydroxyl groups capable of bonding to or reacting with other chemical functionalities. In one embodiment, the inorganic oxide materials include, but are not limited to, silica such as chromatographic grade silica or silica gel, alumina, silica-alumina, zirconia, zirconate, titania and combinations thereof. Magnetically responsive inorganic metal oxides, such as siliceous oxide-coated magnetic particles disclosed in WO 98/31461 (the disclosure of which is incorporated herein in its entirety by reference) may also be used as support material in the present invention. Mixed inorganic metal oxides, e.g. co-gels of silica and alumina, or co-precipitates may also be used as support material.

In one desired embodiment of the present invention, the inorganic metal oxide is silica, more desirably, chromatographic grade silica or silica gel.

Organic materials useful as support material in the present invention include, but are not limited to, synthetic and natural polymeric material. Suitable synthetic polymeric materials include polymethylmethacrylate (MMA), polystyrene-divinylbenzene (PB-DVB), polyacrylamide acrylate and combinations thereof. Suitable nature polymeric materials include polysaccharides such as agarose, cellulose, dextran and combination thereof. It is also within the scope of the invention that the support material may be a hybrid of organic and inorganic material mentioned hereinabove, such as for example, a polymer coated silica.

The support material may be in a physical form of particulates, fibers plates, membranes, monoliths or a combination thereof. Desirably, the support materials are in a physical form of particulates or particles having a substantially spherical or irregular shape. Regardless of the physical form, the solid support, which is an inorganic oxide in a preferred embodiment, typically has a longest dimension (i.e., length, width or diameter) of up to about 150 micrometers (µm). When the support material comprises a plurality of particles having a substantially spherical or irregular shape, the plurality of particles desirably have an average particle diameter ranging from about 1 µm to about 150 µm. In one desired embodiment of the present invention, the support material comprises a plurality particles having a substantially spherical or irregular shape, wherein the plurality of particles have an average particle diameter ranging from about 15 µm to about 120 µm.

A variety of commercially available solid inorganic metal oxides may be used as particulate support material in the present invention. Suitable solid inorganic metal oxides include, but are not limited to, silica particles commercially available from W. R. Grace & Co.-Conn, (Columbia, Md.) under the trade designation DAVISIL®, such as DAVISIL® XWP (extra wide pore) silica media, which are irregular shaped with an average pore size of about 500 Å to about 5000 Å, desirably from about 500 Å to about 2500 Å.

The support may also be in the form of monoliths or membranes (asymmetrical or symmetrical). Inorganic membranes useful as supports in the present invention membranes comprised of metal, carbon, ceramics, metal oxide, and combinations thereof. Suitable polymeric membranes include, but are not limited to, membranes comprised of cellulosic material, nylon, polyether sulfone (PES), polysulfone (PS), polypropylene (PP), polyethylene (PE), polyvinylidene fluoride (PVDF) and combinations thereof.

The surfaces of the above-described support material, particulate as well as non-particulate support materials, are cost effectively and efficiently treated or modified in order to provide one or more of the following features:

(1) polymer chains comprising (i) one or more positive charges thereon, (ii) one or more negative charges thereon, (iii) one or more ionizable functional groups that can form a positive or negative charge via dissociation or association of an atom (e.g., hydrogen) or an ion (e.g., proton), or (iv) any combination of (i) to (iii);

(2) polymer chains covalently bonded directly to sulfur atoms within the thiol groups extending from the support surface (i.e., there are no other atoms positioned between the polymer chain and the sulfur atom of the thiol group);

(3) polymer chains covalently bonded to a surface of the support material thru (i) a second divalent sulfur bond —S—, (ii) a divalent oxygen bond —O— and a divalent silicon bond —Si— with the divalent oxygen bond —O— being positioned between the divalent silicon bond —Si— and the polymer chain, or (iii) both (i) and (ii);

(4) at least one bifunctional second compound extending from the surface of the support material so as to increase the hydrophilicity of the surface;

(5) reduce non-specific, non-selective binding and/or adsorption of non-analyte materials (i.e., non-specific binding of materials other than the target analyte) and ligand-specific analyte materials (i.e., non-specific binding of the target analyte to reactive sites other than reactive sites provided by the one or more ligands) onto the surface of the support material;

(6) less affinity for non-analyte materials (i.e., materials other than the target analyte) due to, for example, the presence of relatively inert R groups on the surface of the support material;

(7) a controlled amount of reactive sites for selectively bonding of one or more analytes to the surface of the support material; and (8) a controlled length of polymer chains extending from the surface of the support material so as to tailor a given polymer chain length to a specific analyte (e.g., when the functionalized support material is used as a chromatographic material).

The functionalized support material of the present invention may comprise, include, consist essentially of or consist of any embodiments disclosed and described herein.

Generally, the functionalized support material comprises a support material; and polymer chains extending from a surface of said support material, said polymer chains being covalently bonded to said surface thru a divalent sulfur bond —S—, wherein said polymer chains comprise (i) one or more positive charges thereon, (ii) one or more negative charges thereon, (iii) one or more ionizable functional groups that can form a positive or negative charge via dissociation or association of an atom (e.g., hydrogen) or an ion (e.g., proton), or (iv) any combination of (i) to (iii).

In some embodiments, the polymer chains of the functionalized support material comprise (i) one or more positive charges thereon, (ii) one or more negative charges thereon, or (iii) both (i) and (ii). In one embodiment, the polymer chains comprise (i) one or more positive charges thereon. In another embodiment, the polymer chains comprise (i) one or more negative charges thereon.

In other embodiments, the polymer chains of the functionalized support material are covalently bonded directly to the thiol groups via the sulfur atom of each thiol group.

In another embodiment, the polymer chains of the functionalized support material comprise polymerized monomers comprising (3-acrylamidopropyl)-trimethylammonium chloride, diallyldimethylammonium chloride, or any combination thereof.

In one embodiment, the polymer chains of the functionalized support material comprise polymerized monomers comprising 2-acrylamido-2-methyl-1-propanesulfonic acid (AMPS), vinylsulfonic acid or any combination thereof.

In other embodiments, the polymer chains of the functionalize support material are covalently bonded to said surface thru (i) a second divalent sulfur bond —S—, (ii) a divalent oxygen bond —O— and a divalent silicon bond —Si— with the divalent oxygen bond —O— being positioned between the divalent silicon bond —Si— and the polymer chain, or (iii) both (i) and (ii).

In some embodiments, the polymer chains of the functionalized support material are also covalently bonded to said surface thru a second divalent sulfur bond —S—. In other embodiments, the polymer chains of the functionalized support are covalently bonded to said surface thru a divalent oxygen bond —O— and a divalent silicon bond —Si— with the divalent oxygen bond —O— being positioned between the divalent silicon bond —Si— and the polymer chain.

In some embodiments, the support material further comprises at least one bifunctional second compound extending from said surface of said support material, each of said at least one bifunctional compound comprising (i) one or more functional groups capable of bonding the bifunctional compound to said surface, and (ii) one or more hydrophilic groups.

In other embodiments, the functionalized support material of any one of the embodiments described hereinabove comprises a covalent bond linkage between said support material and each of said polymer chains, wherein said covalent bond linkage consists of one or more atoms selected from the group consisting of C, O, Si and S.

The functionalized support material of any one of the embodiments described hereinabove, comprises a particulate support material. In some embodiments, the particulate support material comprises inorganic particles. In an embodiment, the particulate support material comprises silica or silica gel particles. In one embodiment, the functionalized support material comprises silica particles having an average particle size, as measured by an average largest particle dimension, ranging from about 12 µm to about 150 µm. The average particle size typically ranges from about 12 µm up to and including about 150 µm, in increments of 1.0 µm, and may be any average particle size between 12 µm and 150 µm (e.g., about 75 µm) or any range of average particle sizes between 12 µm and 150 µm (e.g., from about 55 µm to about 80 µm). In another embodiment, the functionalized support material comprises silica particles having an average particle size, as measured by an average largest particle dimension, ranging from about 20 µm to about 120 µm, and an average pore size of at least 150 Å. The average pore size typically ranges from about 150 Å up to and including about 5000 Å, in increments of 1.0 Å, and may be any average pore size between 300 Å and 4000 Å (e.g., about 2500 Å) or any range of average pore sizes between 500 Å and 3000 Å (e.g., from about 1000 Å to about 2500 Å).

In other embodiments, the particulate support material of the functionalized support material comprises polymeric particles. In one embodiment, the particulate support material comprises polymeric particles selected from the group consisting of poly(methylmethacrylate) resins, agarose resins, and polystyrene copolymers (e.g., poly(styrene/divinyl benzene) (PS-DVB) resins).

II. Methods of Making Functionalized Support Material

The present invention is also directed to methods of making functionalized support material. As discussed above, in one exemplary embodiment, the method of making functionalized support material comprises reacting support material with one or more first reactants so as to form an intermediate product having thiol groups thereon; and polymerizing one or more monomers onto the intermediate product via the thiol groups so as to form polymer chains covalently bonded to the thiol groups. The one or more monomers desirably form polymer chains covalently bonded to the thiol groups, wherein the polymer chains comprise (i) one or more positive charges thereon, (ii) one or more negative charges thereon, (iii) one or more ionizable functional groups that can form a positive or negative charge via dissociation or association of an atom (e.g., hydrogen) or an ion (e.g., proton), or (iv) any combination of (i) to (iii).

Suitable monomers for forming the polymer chains extending from a surface of the support material may include, but are not limited to, 2-acrylamido-2-methyl-1-propanesulfonic acid (i.e., AMPS monomer), acrylic acid, methacrylic acid, N,N-diethylaminoethyl acrylate, (3-acrylamidopropyl)-trimethylammonium chloride, diallyldimethylammonium chloride, or any combination thereof.

As discussed above, in some embodiments, the polymerizing step utilizes a reaction mixture free of organic solvent. In these embodiments, the reaction mixture comprises, consists essentially of or consists of, (i) the herein-described intermediate product having thiol groups thereon, (ii) the one or more monomers, (iii) one or more oxidizing agents such as an inorganic salt, and (iv) deionized water.

In other embodiments, the polymerizing step utilizes a reaction mixture containing one or more organic solvents. In these embodiments, the reaction mixture comprises, consists essentially of, or consists of (i) the herein-described intermediate product having thiol groups thereon, (ii) the one or more monomers, (iii) one or more oxidizing agents or a radical initiator such as an inorganic salt, (iii) one or more organic solvents, and (v) deionized water. Suitable organic solvents, when present, include, but are not limited to, dimethylformamide (DMF), dimethyl sulfoxide (DMSO), N-methylpyrrolidone (NMP). When present, each organic solvent is present in an amount raging from greater than 0 to about 100 weight percent (wt %) based on a total weight of the reaction mixture.

In one exemplary embodiment, the method of making functionalized support material or chromatographic material comprises reacting support material with one or more first reactants so as to form an intermediate product having thiol groups thereon; and polymerizing one or more monomers onto the intermediate product via the thiol groups so as to form polymer chains covalently bonded (e.g., directly) to the thiol groups, the polymerizing step utilizing a reaction mixture comprising, consisting essentially of, or consisting of (i) the intermediate product having thiol groups thereon, (ii) the one or more monomers, (iii) one or more oxidizing agents or a radical initiator such as a bromate-containing salt, (iv) deionized water, and (v) one or more optional organic solvents.

An exemplary reaction scheme for methods of the present invention is shown in FIG. 1. As shown in FIG. 1, in a first step (e.g., a dry bonding step), one or more first reactants in the form of a thiol-containing silane, namely, (3-mercaptopropyl)-trimethoxysilane, reacts with hydroxyl groups along a particle surface of a particulate support material in the form of a silica particle. The resulting intermediate product comprises thiol groups thereon. In a second step, a polymerization step, the resulting intermediate product comprises thiol groups is reacted with one or more monomers in the form of 2-acrylamido-2-methyl-1-propanesulfonic acid (i.e., AMPS monomer) in the presence of potassium bromate salt at a reaction temperature of about 30° C.

As discussed above, in some embodiments, the polymerizing step utilizes a reaction mixture free of organic solvent (e.g., free of toluene, free of DMF, free of DMSO, free of NMP). Further, in some desired embodiments, the polymerizing step utilizes a reaction mixture comprising (i) the intermediate product having thiol groups thereon, (ii) the one or more monomers, (iii) a single oxidizing agent or a radical initiator, for example, in the form of a bromate-containing inorganic salt (e.g., potassium bromate or sodium bromate), and (iv) deionized water.

Although not limited to any particular mechanism, it is believed that the generation of radicals by oxidation of thiols with bromate ions follows the following mechanism:

$$BrO_3^- + RSH \rightarrow BrO_2^- + \cdot OH + RS \cdot$$

$$BrO_2^- + RSH \rightarrow BrO^- + \cdot OH + RS \cdot$$

$$BrO^- + RSH \rightarrow Br^- + \cdot OH + RS \cdot$$

Although not limited to any particular mechanism, it is further believed that the solution phased polymerization, as described in the present invention when a bromate-containing inorganic salt is used as a polymerization catalyst, follows the following kinetics:

$$\text{Polymerization Rate} = k[M][BrO_3^-]^{1/2}[RSH]^{1/2}$$

where [M] is the concentration of the monomer, and [BrO$_3^-$] and [RSH] are the concentrations of the bromate ions and the thiols, respectively.

As shown in the examples below, a variety of polymerization catalysts may be used in the methods of the present invention. Suitable polymerization catalysts/oxidizing agents include, but are not limited to, a cerium (IV) salt such as Ce(SO$_4$)$_2$, a peroxide such as hydrogen peroxide, sodium persulfate (Na$_2$S$_2$O$_8$), sodium perborate (NaBO$_3$), sodium periodate (NaIO$_4$), guanidine nitrate, calcium hypochlorite (Ca(ClO)$_2$), sodium nitrate (NaNO$_3$), a bleach solution (e.g., a 12 wt % sodium hypochlorite solution), and an radical initiator such as the V-50 initiator (i.e., 2,2'-Azobis(2-methylpropanamidine)dihydrochloride commercially available from Wako Specialty Chemicals (Richmond, Va., USA)).

The methods of making functionalized support material result in polymer chains comprise n monomeric units. Typically, n ranges from about 2 to about 1 million monomeric units depending on a number of factors including, but not limited to, the support material, and the ultimate use of the functionalized support material (e.g., as a chromatographic material).

When the functionalized support material is to be used as a chromatographic material, the methods of the present invention provide the ability to tailor a controlled length of polymer chains extending from the surface of the support material depending on a target analyte (e.g., a target protein). In protein purification for strong cation exchange materials, the target proteins can vary in size significantly. For example, egg white lysozyme has a molecular weight of about 15,000 D, while bovine γ-globulin has a molecular weight of about 200,000 D. The methods of the present invention enable optimization of support material pore size (i.e., pore size of silica) and the amount of polymer needed to provide maximum binding of proteins such as lysozyme and γ-globulin. For example, it has been determined that for lysozyme, 70 μm DAVISIL® silica of 1250 Å (D1250) in average pore size, together with a relatively high amount of 2-acrylamido-2-methylpropane sulfonic acid (AMPS) monomer led to high binding, whereas for γ-globulin, D2000 or D2500 silica, of the same particle size, with a relatively low amount of AMPS led to high binding. The following table shows highest binding for the two proteins when compared with commercially available Capto™ S resin from General Electric (GE):

TABLE 1

Tailored Functionalized Silica Particles and Binding Results

| Samples | Silica | Monomer Amount | 5% DBC (mg/ml) |
|---|---|---|---|
| S-Silica 1 | D1250 | 66.7 wt % of Silica | 152 (lysozyme) |
| S-Silica 2 | D2500 | 20 wt % of Silica | 27 (globulin) |
| GE Capto S | n/a | n/a | 130 (lysozyme) |
|  |  |  | 17 (globulin) |

In some embodiments, the methods of the present invention may be carried out using a "one pot" process, wherein the amount of monomer needed for polymerization is significantly reduced. In these embodiments, the method provides an opportunity for cost saving as less than half of a typical amount of the monomer is needed for the polymerization. The ease of process (i.e., no overhead stirrer, and heating is provided by a simple water bath) also adds to cost savings. Performance and maximal binding of globulin to chromatographic material formed using the "one pot" process are shown in the following table:

TABLE 2

Functionalized Silica Particles Formed Using the "One-Pot" Process and Binding Results

| Samples | Silica | Monomer Amount | 5% DBC (mg/ml) |
|---|---|---|---|
| S-Silica 3 | D2000 | 16.7% of Silica | 29 |
| S-Silica 4 | D2500 | 20 wt % of Silica | 26 |

The rationale for the two formulas, although not wishing to be bound by theory, is that due to the large MW size of the surface polymers, certain blockage of pore size by polymers has led to low binding of large proteins with small pore size silica with large amount of polymers on the surface, and therefore for large proteins such as γ-globulin, a large pore size silica with small amount of polymer on the surface provides better binding results. Thus, the formula for optimizing the functionalized support materials so as to provide exceptional binding results is very flexible with the choice of different pore size support materials (e.g., silica having a pore size of from 500 Å to 6000 Å), and amounts of polymers attached (i.e., by varying the amount of monomer used and the amount of polymerization catalyst) varying depending on the target protein (or other bio-target) and its specific size.

The methods for forming (or for making) functionalized support material of the present invention may comprise, consist essentially of, or consist of any of the following additional embodiments:

In general, the method of the invention comprises reacting support material with one or more first reactants so as to form an intermediate product having thiol groups thereon; and polymerizing one or more monomers onto the intermediate product via the thiol groups so as to form polymer chains covalently bonded to the thiol groups, wherein the polymer chains comprise (i) one or more positive charges thereon, (ii) one or more negative charges thereon, (iii) one or more ionizable functional groups that can form a positive or negative charge via dissociation or association of an atom (e.g., hydrogen) or an ion (e.g., proton), or (iv) any combination of (i) to (iii).

In one embodiment of the foregoing method, the polymer chains comprise (i) one or more positive charges thereon, (ii) one or more negative charges thereon, or (iii) both (i) and (ii). In another embodiment of the foregoing methods, the polymer chains are covalently bonded directly to the thiol groups via the sulfur atom of each thiol group.

In some embodiments of the foregoing methods, the support material comprises particulate support material. In one embodiment, the support material comprises inorganic particles. In other embodiments, the support material comprises silica particles. In one embodiments, the support material comprises silica particles having an average particle size, as measured by an average largest particle dimension, ranging from about 12 μm to about 150 μm. The average particle size typically ranges from about 12 μm up to and including about 150 μm, in increments of 1.0 μm, and may be any average particle size between 12 μm and 150 μm (e.g., about 75 μm) or any range of average particle sizes between 12 μm and 150 μm (e.g., from about 55 μm to about 80 μm). In another embodiment, the functionalized support material comprises silica particles having an average particle size, as measured by an average largest particle dimension, ranging from about 20 μm to about 120 μm, and an average pore size of at least 150 Å. The average pore size typically ranges from about 150 Å up to and including about 5000 Å, in increments of 1.0 Å, and may be any average pore size between 300 Å and 4000 Å (e.g., about 2500 Å) or any range of average pore sizes between 500 Å and 3000 Å (e.g., from about 1000 Å to about 2500 Å).

In other embodiments of the inventive method, the support material comprises polymeric particles. In one embodiment the support material comprises polymeric particles selected from the group consisting of poly(methylmethacrylate) resins, agarose resins, and polystyrene copolymers (e.g., poly(styrene/divinyl benzene) (PS-DVB) resins).

In some embodiments of the invention method, one or more first reactants comprise at least one bifunctional first compound comprising (i) one or more functional groups capable of bonding the first compound to the support material, and (ii) one or more thiol groups. In one embodiment, the one or more first reactants comprise at least one thiol-substituted silane. In another embodiment, the one or more first reactants comprise (3-mercaptopropyl)-trimethoxysilane.

In some embodiments of the invention method, the one or more first reactants comprise (1) at least one bifunctional linking compound comprising (i) one or more functional groups capable of bonding the linking compound to the support material, and (ii) one or more additional functional groups capable of covalently bonding with a compound comprising one or more thiol groups, and (2) at least one bifunctional thiol-containing compound comprising (i) one or more functional groups capable of covalently bonding with the one or more additional functional groups of the linking compound, and (ii) one or more thiol groups. In one embodiment, each of the one or more additional functional groups independently comprises an epoxy group, an amine group, or any combination thereof. In another embodiment, the one or more first reactants comprise at least one epoxy silane. In yet another embodiment, the one or more first reactants comprises (3-glycidoxypropyl)-trimethoxysilane. In another the one or more first reactants comprise 1,2-ethanedithiol.

In other embodiments the one or more first reactants further comprise at least one bifunctional second compound comprising (i) one or more functional groups capable of bonding the second compound to the support material, and (ii) one or more hydrophilic groups. In one embodiment, each of the one or more hydrophilic groups independently comprises a hydroxyl group, a carbonyl group, a carboxyl group, an amino group, or any combination thereof. In one embodiment, the one or more first reactants further comprise at least one additional silane having one or more hydrophilic groups thereon. In another embodiment, the one or more first reactants further comprises 2-[methoxy(polyethyleneoxy)propyl]-trimethoxysilane.

In other embodiments, the one or more first reactants result in a covalent bond linkage between the support material and the polymer chains, wherein the covalent bond linkage consists of one or more atoms selected from the group consisting of C, O, Si and S. In other embodiments, the one or more monomers comprise (i) a first set of monomers with each monomer having no charge thereon, (ii) a second set of monomers with each monomer having a positive charge thereon, (iii) a third set of monomers with each monomer having a negative charge thereon, or (iv) any combination of (i) to (iii).

In some embodiments, the one or more monomers comprise a first set of monomers with each monomer having no charge thereon.

In other embodiment, the one or more monomers comprise a first set of monomers with each monomer having no charge thereon, and at least a portion of the monomers within the first set comprise one or more polar substituents thereon. In one embodiment, the one or more monomers comprise acrylic acid, methacrylic acid, N,N-diethylaminoethyl acrylate, or any combination thereof.

In other embodiments, the one or more monomers comprise a second set of monomers with each monomer having a positive charge thereon. In one embodiment, the one or more monomers may comprise (3-acrylamidopropyl)-trimethylammonium chloride, diallyldimethylammonium chloride, or any combination thereof.

In other embodiment, the one or more monomers comprise a third set of monomers with each monomer having a negative charge thereon. In one embodiment, the one or more monomers comprise 2-acrylamido-2-methyl-1-propanesulfonic acid (AMPS), vinylsulfonic acid, or any combination thereof.

In some embodiments, the said polymerizing step utilizes a reaction mixture free of organic solvent. In other embodiments, the polymerizing step utilizes a reaction mixture comprising one or more organic solvents.

In some embodiments, the polymerizing step utilizes a reaction mixture comprising, consisting essentially of or consisting of (i) the intermediate product having thiol groups thereon, (ii) the one or more monomers, (iii) one or more oxidizing agents or radical initiators, (iv) deionized water, and optionally (v) one or more organic solvents.

In some embodiments, the polymerizing step utilizes one or more oxidizing agents selected from the group consisting of a bromate ion-containing salt, a cerium (IV) salt (e.g., $Ce(SO_4)_2$), a peroxide (e.g., hydrogen peroxide), sodium persulfate ($Na_2S_2O_8$), sodium perborate ($NaBO_3$), sodium periodate ($NaIO_4$), guanidine nitrate, calcium hypochlorite ($Ca(ClO)_2$), sodium nitrate ($NaNO_3$), a bleach solution (e.g., a 12 wt % sodium hypochlorite solution), or an azo initiator such as 2,2'-Azobis(2-methylpropionamidine)dihydrochloride, and combinations thereof. In one embodiment, the one or more oxidizing agents comprises a bromate ion-containing salt. In another embodiment, the one or more oxidizing agents comprises sodium bromate. In yet another embodiment, the one or more oxidizing agents comprises potassium bromate.

In some embodiments, the reaction mixture consists of (i) the intermediate product having thiol groups thereon, (ii) the one or more monomers, (iii) a single oxidizing agent consisting of the bromate ion-containing salt, and (iv) deionized water.

In some embodiments, the polymerizing step is conducted at a temperature of from about 10° C. to about 80° C. In other embodiments, the polymerizing step is conducted at a temperature of from about 30° C. to about 70° C.

In some embodiments, the polymerizing step is conducted at the temperature for a period of up to about 3 hours. In other embodiments, the polymerizing step is conducted at the temperature for a period of about 2 hours. In some embodiments, the polymerizing step is conducted under a nitrogen or argon gas blanket.

In other embodiments, the invention method further comprises washing the intermediate product prior to said polymerizing step so as to remove any unreacted or unattached first reactants. In one embodiment, the method further comprises washing the intermediate product prior to said polymerizing step so as to remove any unreacted or unattached first reactants, said washing step comprising contacting the intermediate product with an organic solvent selected from methanol, acetone, isopropyl alcohol (IPA) or any combination thereof. In another embodiment, the method comprises washing the intermediate product prior to said polymerizing step so as to remove any unreacted or unattached first reactants, said washing step comprising contacting the intermediate product with deionized water. In other embodiments, the method further comprises filtering the intermediate product from a washing solution following said washing step.

In some embodiments, the method further comprises drying the intermediate product following said filtering step.

In other embodiments, the method further comprises washing the functionalized support material following said polymerizing step. In one embodiment, the washing step following said polymerizing step comprises contacting the functionalized support material with (i) one or more wash solutions consisting of a salt solution, (ii) one or more wash solutions consisting of deionized water, or (iii) any combination of (i) and (ii). In another embodiment, the washing step following said polymerizing step comprises contacting the functionalized support material with (i) a first wash solution consisting of a sodium chloride salt solution, (ii) a second wash solution consisting of a sodium bicarbonate salt solution, (iii) a third wash solution consisting of a sodium chloride salt solution, and (iv) a fourth wash solution consisting of deionized water.

In other embodiments, the method further comprises filtering the functionalized support material following each washing step following said polymerizing step or after one or more washing steps following said polymerizing step. In one embodiment, the method comprises drying the functionalized support material following one or more filtering steps.

In other embodiments, the polymerizing step comprises utilizing a desired amount of the one or more monomers so as to form polymer chains having a tailored length depending on a target analyte (e.g., a target protein).

III. Intermediate Products Formed in Methods of Making Functionalized Support Material It should be noted that the present invention is also directed to intermediate products having thiol groups thereon formed by the reacting step of the above-described methods. Intermediate product embodiments may include any intermediate product having thiol groups thereon formed by the reacting step of the method of any one of embodiments discussed hereinabove.

IV. Columns or Cartridges in Combination with Functionalized Support Material, and Methods of Making and Using the Same The present invention is directed to chromatography columns or cartridges, such as in a high pressure liquid chromatography (HPLC) column or a fast protein liquid chromatography (FPLC) column comprising functionalized support materials of the invention. The present invention is further directed to functionalized support material, and chromatography columns or cartridges, in general, in combination with or comprising functionalized support material. The present invention is even further directed to methods of using functionalized support material, for example, as media in a chromatography column or cartridge for analysis of test samples, including complex mixtures (e.g., mixtures containing biological components), which potentially contain one or more analytes.

In exemplary embodiments, the present invention comprises chromatography columns or cartridges comprising any (i) one or (ii) combination of two or more of the herein-described functionalized support materials; methods of making chromatography columns and cartridges in combination and/or comprising any (i) one or (ii) combination of two or more of the herein-described functionalized support materials; and methods of using any (i) one or (ii) combination of two or more of the herein-described functionalized support materials, for example, in methods of analyzing a test sample.

The present invention may further comprise, include, consist essentially of, or consist of any of the following additional embodiments:

In some embodiments, a chromatography column or cartridge suitable for use in a chromatography apparatus is provided, said chromatography column or cartridge comprising a functionalized support material or a chromatographic material of any one of the embodiments described hereinabove.

In one embodiment, a chromatography apparatus comprises the chromatography column or cartridge as described in the present invention. Other embodiments include a method of analyzing or separating or purifying a sample or a mixture, said method comprising the step of bringing the sample into contact with a functionalized support material or a chromatographic material in accordance with the invention.

In other embodiments, a method of analyzing or separating or purifying a sample or a mixture containing at least one biological compound comprises the step of bringing the sample containing at least one biological compound into contact with the functionalized support material or the chromatographic material of the invention. In one such embodiment, the at least one biological compound comprises a virus, a vaccine, an antibody, a protein, a peptide, a polypeptide, a non-peptidyl compound, a polyene macrolide, a terpene, an alkaloid, a carbohydrate, an oligonucleotide, a derivative thereof, an analogue thereof, or any combination thereof.

The present invention is described above and further illustrated below by way of examples, which are not to be construed in any way as imposing limitations upon the scope of the invention. The examples are given as specific illustrations of the claimed invention. It should be understood, however, that the invention is not limited to the specific details set forth in the examples. It is to be clearly understood that resort may be had to various other embodiments, modifications, and equivalents thereof which, after reading the description herein, may suggest themselves to those skilled in the art without departing from the spirit of the present invention and/or the scope of the appended claims.

All parts and percentages in the examples as well as the remainder of the specification which refers to solid compositions or concentrations are by weight unless otherwise specified. However, all parts and percentages in the examples as well as the remainder of the specification referring to gas compositions are molar or by volume unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited.

EXAMPLES

The following examples described processes for modifying the surfaces of media, including silica and polymeric resins, using the thiol oxidation polymerization chemistry of the present invention. It should be noted that although silica and poly(methylmethacrylate) particles are used in the following examples, other types of particles (or other support materials as discussed above) and particle surfaces (or other support material surfaces) could be modified using similar process.

One example below relates to porous inorganic media, a silica based ion exchange material, formed via a process consisting of two main steps: (1) bonding of silica surface with thiol group containing methoxysilane to form an initially bonded intermediate; and (2) free radical polymerization of ionic monomer(s), through the introduction of oxidizing agents such as sodium bromate, in the presence of the initially-bonded silica intermediate to generate surface radicals. The surface radicals initiated free radical polymerization of the ionic monomer(s) to form either strong cation exchange media (i.e., referred to herein as "S-silica"), or anion exchange media (i.e., referred to herein as "Q-silica").

In another example, the silica particle surface was functionalized with both thiol containing groups and polyethylene glycol containing groups, and the surface was further modified with ionic polymers through free radical polymerization.

In still another example, poly(methylmethacrylate) (PMMA) resin particles having surface epoxy groups thereon were treated with 1,2-ethanedithiol to introduce surface thiol groups. In this example, one SH group of the 1,2-ethanedithiol reacts and opens the epoxy ring on the PMMA particle surface, and the other SH group of 1,2-ethanedithiol is available for the next step polymerization reaction, followed by oxidative free radical polymerization.

In one example below for producing S-silica, the monomer utilized was 2-acrylamido-2-methyl-1-propanesulfonic acid (AMPS). In another example below for producing Q-silica, the monomer utilized was (3-acrylamidopropyl)-trimethylammonium chloride. In still another example below for producing a charge-neutral particle surface, the monomer was methacrylic acid. In a final example below, the monomer used was N,N-diethylaminoethyl methacrylate.

Many different types of porous particles were functionalized using the disclosed methods. In some of the examples below, silica gels were utilized, wherein the silica gels have a 70 micron median particle size with median pore sizes of 250, 500, 800, 1000, 1250, 1500, 2000, 2500 and 3000 Angstroms (Å), etc. The silica gels were prepared using the following procedure: 190 g of a 19 wt % sulfuric acid solution was placed in a reactor equipped with an overhead stirrer and chilled to 5° C. Separately, 263 g of a solution of sodium silicate (22.9 wt % $SiO_2$) was also chilled to 5° C. Subsequently, the sodium silicate solution was added to the sulfuric acid solution via a pump at such a rate as to add the full quantity of silicate in 15 minutes. During the addition step, the temperature was maintained at 5° C. After the addition was completed, the reactor was warmed to room temperature and the contents were allowed to gel without stirring. Upon gelation, the gel mass was cut in small pieces and submerged in water, in order to remove the sodium sulfate formed during the reaction.

The level of sodium sulfate remaining in the material was periodically checked, as wash water was drained and fresh water was added to the gel. When the level fell below 1 wt %, the gel was suspended in water, the pH of the liquid was adjusted to pH=9.7, and the solution was heated to 67° C. The temperature was maintained for 20 hours and 20 minutes. At the end of the heating period, the gel was recovered by filtration and dried in a 160° C. oven until the moisture content of the gel was less than about 5% by weight.

The silica gel thus obtained had a nitrogen Brunauer-Emmett-Teller (BET) surface area of 325 $m^2$/g and a nitrogen pore volume of 1.24 cc/g. Assuming cylindrical pores and using the equation:

$$\text{Pore Size (Å)}=40000 \times PV/SA,$$

the material exhibited a pore size of 153 Å. Subsequently, the gel was milled to the desired particle size (e.g., 70 microns) using an Air Classifying Mill (ACM) and then hydrothermally treated in an autoclave at 300° C. until the desired pore size is achieved.

The particle sizes reported in the examples were determined by light scattering using a Malvern Mastersizer 2000 available from Malvern Instruments Ltd. per ASTM B822-10. Pore size distributions were measured by mercury intrusion using an Autopore IV 9520 available from Micromeritics Instrument Corporation. Pore volumes referenced herein represented mercury intrusion into pores 10,000 Å and below. Pore size distributions were also measured by nitrogen sorption (i.e., the BJH (Barrett-Joyner-Halenda) method) using a Tristar 3000 also available from Micromeritics Instrument Corp. BJH surface areas were calculated for pores in the range of 20 to 3800 Å. BET surface areas were also obtained from the nitrogen sorption analysis. Elemental analyses of carbon and sulfur content were conducted using a LECO Carbon and Sulfur Analyzer SC-632 available from LECO Corp. Average molecular weight was determined by GPC analysis using a GPCV 2000 with RI and Viscometric Detection available from Waters Corp. The purity of the silica was measured by inductively coupled plasma (ICP) using an ICPE-9000 available from Shimadzu Corp.

The static binding tests were performed using lysozyme (S-silica) or BSA (bovine serum albumin) (Q silica) (25 mg/ml concentration in buffer) at pH 7.0 with 50 mM phosphate buffer or pH 8.0 with 50 mM Tris HCl buffer. The binding/washing buffers were (i) pH 7.0 with 50 mM phosphate buffer or (ii) pH 8.0, 50 mM Tris-HCl buffer. The elution buffers were (i) pH 7.0 with 50 mM phosphate buffer or (ii) pH 8.0, 50 mM/Tris-HCl/1 M NaCl.

Oven dried silica samples were weighted into vials, and then protein solutions in binding buffer were added. After overnight adsorption, the samples were centrifuged and supernatant separated and discarded. The silica samples were washed three times with washing buffer with centrifugation and separation. After the washing steps, elution buffer was added and the elution was repeated a second time.

The UV/Vis adsorption was measured for the combined elution solution at 280 um using a Genesys 10S Bio UV-Vis spectrophotometer available from Thermo Fisher Scientific Inc. The binding capacities were calculated based on protein absorption coefficients and the densities of the media.

The dynamic binding tests (DBC) were performed using Omni glass columns with 0.66 cm diameter. For 2 ml of column, the column length was around 5.8 cm. Media samples were de-fined with DI water, and then the column was slurry packed with Akta FPLC at about 4000 cm/h linear velocity. For the breakthrough curve, (i) lysozyme protein in pH 7.0, 50 mM phosphate buffer or (ii) BSA protein in pH 8.0, 50 mM Tris-HCl buffer were passed through a column with Akta at about 500 or 1000 cm/h. UV-Vis signals at 280 run were measured using a UV900 available from General Electric, and chromatograms were recorded and plotted with Microsoft Excel. 5% of breakthrough points were generally used to calculate dynamic binding capacity.

Examples 1-5

Figure 2:
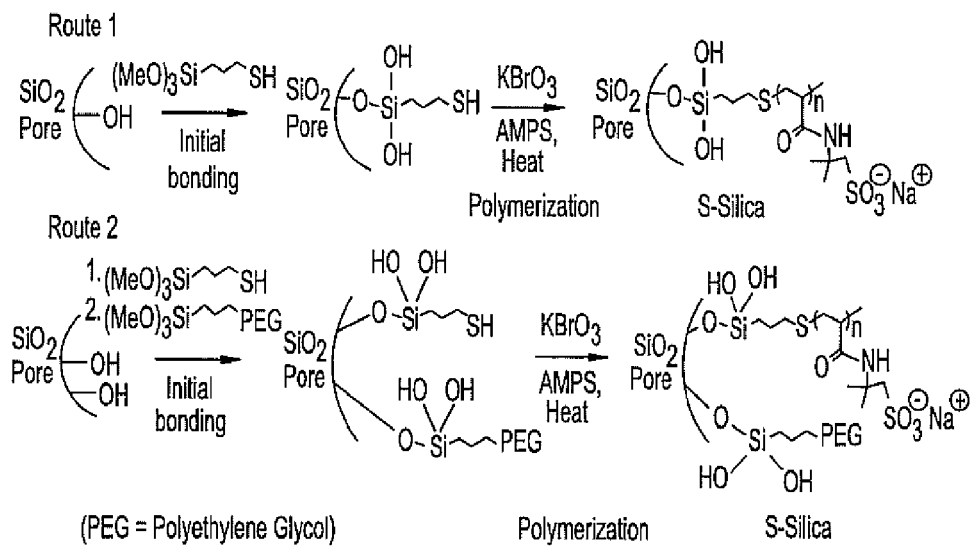
FIG. 2 provides an exemplary reaction scheme for preparing functionalized support material or chromatographic material of the present invention as described in Examples 1-5 below.

As shown in FIG. 2, two different routes were utilized to introduce polymer chains containing anionic sulfonic acid groups onto the surface of silica particles. The first route involved initial bonding of thiol groups by reacting (3-mercaptopropyl)trimethoxysilane (thiol silane), followed by polymerization. The second route involved two surface modifying silanes: (i) thiol silane and (ii) 2-[methoxy(polyethyleneoxy)propyl]-trimethoxysilane (PEG silane) available from Gelest, Inc.

the silica was washed with 5×500 ml of DI water and filtered. After drying, carbon and sulfur contents of the silica were evaluated.

Polymerization

A 500 ml three-necked round bottom flask was equipped with an overhead mechanical stirrer with gas tight fitting, a nitrogen gas inlet and outlet, and heating mantle with thermal couple feedback. The initially bonded silica, 30 g, AMPS monomer (amounts described in Table 1 below), and 200 ml of deionized (DI) water were first charged into the flask. The system was stirred and bubbled with nitrogen for 20 minutes. Then, sodium bromate salt (amounts described in Table 1) was added.

The mixture was graduated heated to 50-60° C. The mixture was kept at constant high temperature for 2 hours with overhead stirring. The flask was then allowed to cool down to room temperature. The mixture was poured into 600 ml of 5% NaCl solution in a beaker. The flask was rinsed with DI water to completely move the residual silica inside the flask. After the mixture was stirred with overhead stirrer for a few minutes, the silica was allowed to settle and the top aqueous layer was separated by decant.

To the silica was added 500 ml of saturated sodium bicarbonate solution and the mixture was stirred for 10 minutes, and then the aqueous solution was separated by settling and decant. The silica was washed three times with 500 ml 5% NaCl, and three times with 500 ml DI water, with each wash followed with filtration under vacuum. The sample was left in air to dry except that a small amount of silica was dried at 90° C. overnight and then submitted for elemental analysis of carbon and sulfur content. The results are listed in Table 3 below:

TABLE 3

Functionalized Silica Particle Results

| Ex. | Silica Pore Size | Initial bond route | C % from initial bonding | S % from initial bonding | Monomer amount (g) | Bromate amount (g) | Rxn Temp (° C.) | Final C % | Final S % | DEC (lysozyme) (mg/ml) |
|---|---|---|---|---|---|---|---|---|---|---|
| 1 | 1000 | 1 | 0.78 | 0.48 | 60 | 1 | 50 | 2.86 | 1.19 | 141 |
| 2 | 1250 | 1 | 1.08 | 0.60 | 60 | 1 | 50 | 2.89 | 1.06 | 139 |
| 3 | 1500 | 2 | 1.03 | 0.47 | 60 | 1 | 50 | 4.09 | 1.51 | 144 |
| 4 | 2000 | 2 | 1.65 | 0.50 | 60 | 0.5 | 50 | 7.17 | 2.77 | 95 |
| 5 | 1250 | 2 | 1.37 | 0.57 | 63 | 1.25 | 60 | 4.88 | 1.40 | 148 |

The main benefit for the second route, as described in the examples, was that the initially bonded silica was more hydrophilic and could be washed with water, while for the first one, some organic solvent, such as methanol or acetone, was used for clean-up and removal of unreacted/unattached silane reagents.

Initial Bonding, Route 1

100 grams of silica was rolled and mixed with 5 grams of (3-mercaptopropyl) trimethoxysilane in a 2 L round bottom flask on a rotavap (i.e., a rotary evaporator) at room temperature for 16 hours. Then, the silica was washed with 4×400 ml of methanol and filtered. After drying, carbon and sulfur contents of the silica were evaluated.

Initial Bonding, Route 2

100 grams silica was rolled and mixed with 5 grams of (3-mercaptopropyl) trimethoxysilane in a 2 L round bottom flask on a rotavap at room temperature for 5 hours, and then 5 grams of 2-[methoxy(polyethyleneoxy(propyl)] trimethoxysilane was added and the mixture was rolled and mixed for 16 hours (overnight) at room temperature. Then, Example 6

Figure 3:
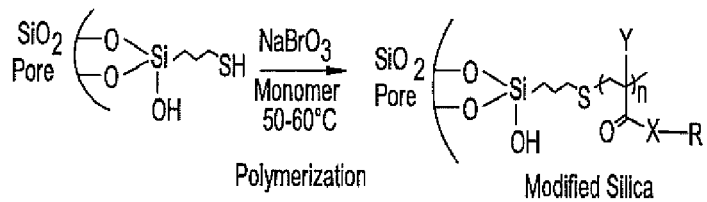
FIG. 3 provides an exemplary reaction scheme for preparing functionalized support material or chromatographic material of the present invention as described in Examples 6-8 below.

The following example utilized a reaction scheme as shown in FIG. 3. 25 grams of initially bonded silica having a 1000 Å median pore size, and a 75 μm average particle size was made as discussed above, but only thiol silane was used in the initial bonding step. (Elemental analysis of the bonded material showed that C=0.95%, S=0.53%.) The intermediate product (i.e., silica particles with thiol groups thereon) was mixed with 35 grams of (3-acrylamidopropyl)-trimethylammonium chloride (75% aqueous solution, available from TCI America), 2.31 grams of diallyldimethylammonium chloride (65% solution, available from Aldrich), and 200 ml of DI water in a 500 ml three necked round bottom flask using a setup as described in Examples 1-5.

After removing air from the system with nitrogen bubbling for 20 minutes, 1.0 grams of potassium bromate was added. The mixture was stirred and gradually heated to 65° C. and reacted at 65° C. for 2 hours. After the reaction, the mixture was cooled to room temperature, and washed with 3×500 ml of 5% NaCl, and 3×500 ml of DI water with filtration. The carbon and sulfur contents for the dried sample were 5.42% and 0.48%, respectively.

Example 7

As shown in FIG. 3, 30 grams of initially bonded silica having a 1000 Å median pore size, and a 75 μm average particle size (i.e., the same as in Example 6) was mixed with 30 gram of methacrylic acid and 150 grams of DI water. The polymerization reaction was conducted as described in Example 6. The final carbon content of the sample after drying was 18.87%.

Example 8

As shown in FIG. 3, 30 grams of initially bonded silica having a 1000 Å median pore size, and a 75 μm average particle size (i.e., the same as in Example 6) was mixed with 30 gram of N,N-diethylaminoethyl acrylate (available from Aldrich) and 150 grams of DI water. The polymerization reaction was conducted as described in Example 6. The final carbon content of the sample after drying was 19.29%.

Example 9

Figure 4:
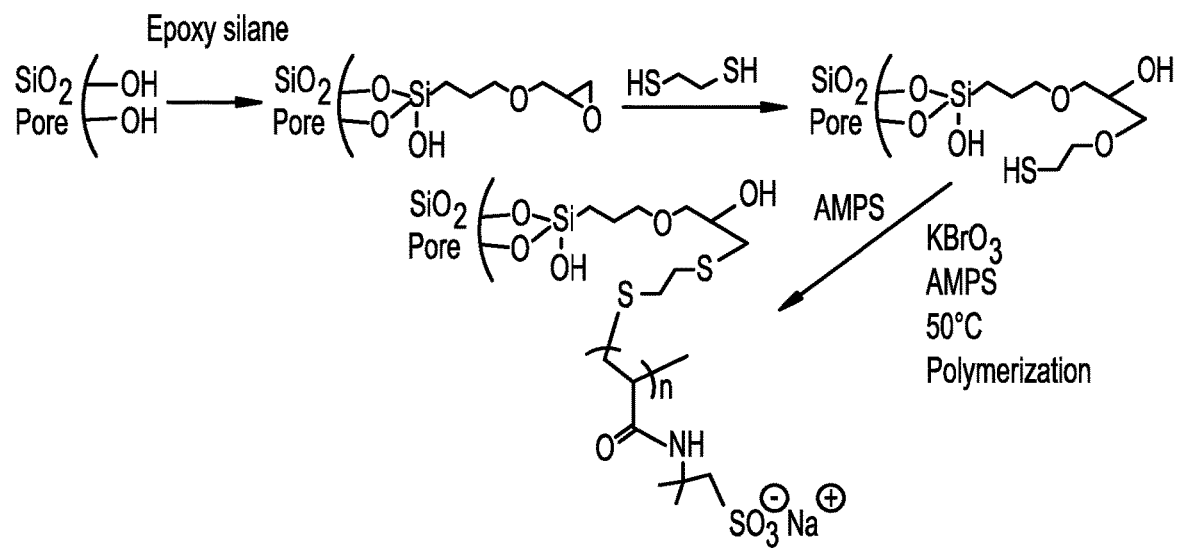
FIG. 4 provides an exemplary reaction scheme for preparing functionalized support material or chromatographic material of the present invention as described in Example 9 below.

The following example utilized a reaction scheme as shown in FIG. 4. As shown in FIG. 4, 65 grams of silica having a 1000 Å median pore size, and a 75 μm average particle size was initially bonded with 9 grams of (3-glycidoxypropyl)-trimethoxysilane (available from Aldrich). After overnight rolling, the treated silica was washed with 5×500 ml of DI water and filtered. A dried sample was determined to have carbon content of 1.18%.

Half of the above, wet silica was mixed with 0.50 g of 1,2-ethanedithiol in 170 ml of DI water. The mixture was stirred and heated to 60° C. for 2 hours, and then 1 ml of concentrated HCl was added. The mixture was mixed for another hour and then allowed to cool to room temperature. Then, 60 grams of AMPS monomer was added. The polymerization was carried in a three necked flask using a similar set up as described in Examples 1-5. After 20 minutes of nitrogen bubbling, 2 grams of potassium bromate was added.

The temperature of the stirred mixture was raised to 60° C. and kept at 60° C. for 2 hours and then the reaction mixture was washed and filtered with 1×500 ml of 10% NaCl, 1×500 ml saturated $NaHCO_3$, 3×500 ml 5% NaCl, and 3×500 ml DI water. It was determined that the final dried sample had a carbon content of 3.11% and sulfur content of 1.19%. Lysozyme DBC was measured to be 74 mg/ml.

Example 10

Figure 5:
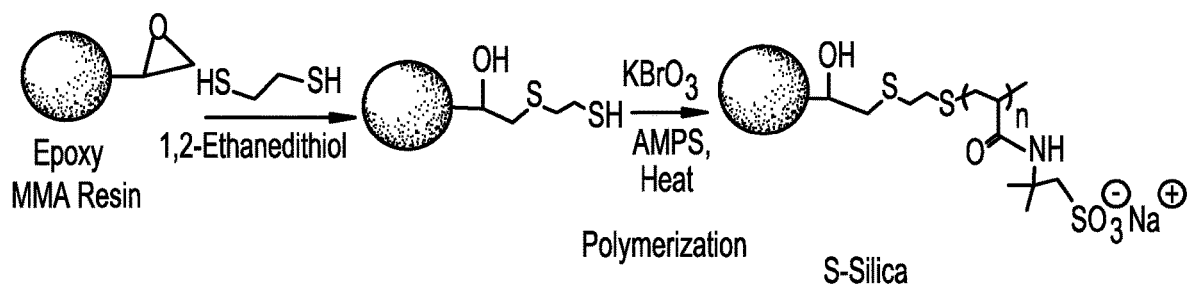
FIG. 5 provides an exemplary reaction scheme for preparing functionalized support material or chromatographic material of the present invention as described in Example 10 below.

The following example utilized a reaction scheme as shown in FIG. 5. Poly(methyl methacrylate) (PMMA) resin particles (100 μm average particle size) having surface epoxy groups thereon were purchased from Resindion (Rome, Italy). To a 1 L three necked round bottom flask, equipped with thermo couple, overhead stirrer, and nitrogen inlet and outlet was added 40 grams (dry based) of the PMMA resin and 0.53 g of 1,2-ethanedithiol, and 100 ml of DI water. The mixture was stirred at room temperature for 20 minutes, and then 10 ml of concentrated HCl was added. The whole mixture was stirred for another 10 minutes and then the temperature of the mixture was raised to, and held at, 60° C. for 1 hour. After cooling to room temperature, the resin was filtered and washed with DI water (3×500 ml) and let dry in air.

20 grams of the above dried resin was mixed with 60 grams of AMPS silica, and 200 g of DI water. The polymerization was carried out in a manner as described in Examples 1-5, with 1.0 gram of $KBrO_3$, at 50° C. for 2 hours. After washing and filtration (similar process as described in other examples), the clean material was evaluated for lysozyme binding. It was determined the DBC was 140.8 mg/ml of lysozyme in pH 7.0 50 mM phosphate buffer.

The present invention was further exemplified via alternative polymerization processes as discussed in the examples below:

One Pot Process, 30 g Scale Reactions:

In a 250 ml Erlenmeyer flask was place 30 g of thiol/PEG modified, dried silica (see, for example, FIG. 2, Route 2), and to this was added pre-determined amounts of AMPS monomer and 95 ml of DI water. Argon gas was bubbled into the mixture. After 20 minutes of bubbling, a 5 ml solution of sodium bromate (0.2 g) was added to the mixture. The top of the flask was quickly sealed with two layers of parafilm to prevent air from getting into the flask. The flask was gradually heat to 65° C. with water bath and kept at 65° C. for 2 hours. During this period, the flask was gently shaken to mix occasionally. After the reaction, the flask was allowed to cool down to room temperature.

The mixture was poured into 300 ml of 5% NaCl solution in a beaker. The flask was rinsed with 10% NaCl solution to completely move the residual silica inside the flask. After the mixture was stirred with overhead stirrer for a few minutes, the silica was allowed to settle and the top aqueous layer was separated by decant. To the silica was added 200 ml of saturated sodium bicarbonate solution and the mixture was stirred for 10 minutes, and then the aqueous solution was separated by settling and decant. The silica was washed three times with 500 ml 5% NaCl and three times with 500 ml DI water, each time followed with filtration under vacuum. The sample was left in air to dry except that a small amount of silica was dried at 90° C. overnight and then submitted for elemental analysis of carbon and sulfur content.

One Pot Process, 100 g Scale Reactions:

In a 500 ml round bottom flask was charged 100 g of thiol/PEG modified, dried silica (see again, for example, FIG. 2, Route 2), pre-determined amounts of AMPS monomer and 320 ml of DI water. The flask was placed onto a rotavap and the whole system was flashed with argon gas for 30 minutes. After that, 0.7 g of sodium bromate in 15 ml of DI water was added through a syringe with a long needle. The whole system was kept under argon gas while the flask was rotated and gradually heated to 60° C. with a water bath. After 2 hours, the flask was allowed to cool down to room temperature.

The mixture was then poured into 600 ml of 5% NaCl solution in a beaker. The flask was rinsed with 10% NaCl solution to completely move the residual silica inside the flask. After the mixture was stirred with overhead stirrer for a few minutes, the silica was allowed to settle and the top aqueous layer was separated by decant. To the silica was added 600 ml of saturated sodium bicarbonate solution and the mixture was stirred for 10 minutes, and then the aqueous solution was separated by settling and decant. The silica was washed three times with 600 ml 5% NaCl and three times with 600 ml DI water, each time followed with filtration under vacuum. The sample was left in air to dry except that a small amount of silica was dried at 90° C. overnight and then submitted for elemental analysis of carbon and sulfur content.

Examples 11 and 12

The median pore size of silica and the amounts of AMPS monomer used in the reaction have significant influence on the binding capacity of large protein γ-globulin. Examples 11 and 12, made with the process at 30 g scale, had large binding capacity for γ-globulin as shown in Table 4 below:

TABLE 4

Functionalized Silica Particles and γ-Globulin Binding Results

| Example | Pore size of silica (Å) | Monomer amount (g) | S % gain after the reaction | γ-Globulin 5% DBC (mg/ml) |
|---|---|---|---|---|
| 11 | 2000 | 6 | 0.15 | 29.3 |
| 12 | 2500 | 6 | 0.13 | 28.7 |

Examples 13-23

The following examples show that other alternative oxidizing agents may be used to successfully make functionalized support materials capable of providing effective binding capacities for target proteins.

In these examples, fixed amounts of silica (30 g) and water were used in the processes as described above. In place of sodium bromate, other catalysts (note, 5 ml of water was used to dissolve the catalysts in case they are solids) were added after 20 minutes of argon bubbling. Other conditions were the same as described in Examples 11-12.

The amounts of polymers attached were presented in the amount of S % gain, and the dynamic binding capacities for lysozyme (Ly) and γ-globulin (Gl) were listed in Table 5 below:

TABLE 5

Functionalized Silica Particles Formed Via Various Catalysts and Binding Results

| Example No. | Catalyst | Catalyst Amount (g) | S % Net Gain | 5% Ly DBC (mg/ml) | 5% Gl DBC (mg/ml) |
|---|---|---|---|---|---|
| 13 | Ce(SO$_4$)$_2$ | 1.0 | 2.01 | 128.1 | 12.1 |
| 14 | Ce(SO$_4$)$_2$ | 2.0 | 0.68 | 91.3 | 32.1 |
| 15 | 30% H$_2$O$_2$ | 1.0 | 0.99 | 98.9 | 7.1 |
| 16 | Na$_2$S$_2$O$_8$ | 0.30 | 0.47 | 76.3 | 8.6 |
| 17 | NaBO$_3$ | 0.75 | 0.60 | 86.4 | 11.6 |
| 18 | NaIO$_4$ | 0.40 | 0.23 | 47.9 | 26.9 |
| 19 | Guanidine Nitrate | 0.23 | 0.29 | 61.1 | 23.2 |
| 20 | Ca(ClO)$_2$ | 2.0 | 0.17 | 70.5 | 18.1 |
| 21 | NaNO$_3$ | 0.16 | 0.26 | 51.1 | 23.7 |
| 22 | 12% bleach | 2.0 | 0.17 | 39.6 | 23.8 |
| 23 | V50 initiator | 0.25 | 0.34 | 61.0 | 20.3 |

In examples 13-22, surface thiol groups were oxidized by oxidizing groups other than bromate ions, generating thiol radicals. Polymerization started from the surface thiol radicals.

In the case of example 23, V-50 initiator, an azo initiator, was used and the reaction followed at high temperature after the radicals were generated from the breakage of the nitrogen-carbon bond. The thiol radicals were generated by hydrogen abstraction of the surface thiol groups by the radicals formed. Thus, the polymerization started from the surface thiol radicals.

It should be understood that the foregoing description and examples relate to exemplary embodiments of the present invention and that modifications may be made without departing from the spirit and scope of the invention as set forth in the following claims. It should also be understood that ranges of values set forth above inherently include end values, as well as all incremental values and ranges therebetween. For example, a particle size of from 0.1 microns (μm) to about 1000 μm includes (1) end points 0.1 μm and 1000 μm, (2) all individual particle sizes between end points 0.1 μm and 1000 μm, in any increment (e.g., 0.1 μm, so 0.2 μm, 0.3 μm, . . . 999.8 μm, and 999.9 μm, etc.), and (3) any range of particle sizes between end points 0.1 μm and 1000 μm (e.g., from about 100.0 μm to about 247.3 μm, etc.).

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for forming chromatographic material, said method comprising:
   reacting silica particles with one or more first reactants to form an intermediate product comprising thiol groups, the one or more first reactants comprising (A) (i) at least one epoxy silane and (ii) 1,2-ethanedithiol, or (B) 3-mercaptopropyl-trimethoxysilane; and
   polymerizing one or more monomers onto the intermediate product via the thiol groups to form polymer chains covalently bonded to the thiol groups, said polymerizing step comprising utilizing a reaction mixture of (i) the intermediate product comprising thiol groups, (ii) the one or more monomers, and (iii) an oxidizing agent comprising a bromate ion-containing salt,
   wherein the one or more monomers comprise: 2-acrylamido-2-methyl-1-propanesulfonic acid, vinylsulfonic acid, or any combination thereof; or 2-acrylamido-2-methyl-1-propanesulfonic acid, methacrylic acid, acrylic acid, N,N-diethylaminoethyl acrylate, (3-acrylamidopropyl)-trimethylammonium chloride, diallyldimethylammonium chloride, or any combination thereof.

2. The method of claim 1, wherein the polymer chains are covalently bonded directly to the thiol groups via the sulfur atom of each thiol group.

3. The method of claim 1, wherein the one or more first reactants comprise (i) at least one epoxy silane and (ii) 1,2-ethanedithiol.

4. The method of claim 1, wherein the one or more first reactants comprise (i) 3 mercaptopropyl-trimethoxysilane and (ii) 2-[methoxy(poly-ethyleneoxy)propyl]-trimethoxysilane.

5. The method of claim 1, wherein said polymerizing step comprises utilizing an amount of the one or more monomers so as to form polymer chains having a tailored length depending on a target analyte.

6. The method of claim 1, wherein the bromate ion-containing salt comprises potassium bromate or sodium bromate.

7. The method of claim 3, wherein the bromate ion-containing salt comprises sodium bromate.

8. The method of claim 1, wherein said polymerizing step comprising utilizing a reaction mixture of (i) the intermediate product comprising thiol groups, (ii) the one or more monomers, (iii) the bromate ion-containing salt, and (iv) deionized water; and the reaction mixture is free of organic solvent.

9. The method of claim 3, wherein the at least one epoxy silane comprises (3-glycidoxypropyl)-trimethoxysilane.

10. A method for forming chromatographic material, said method comprising:
reacting support material with one or more first reactants to form an intermediate product comprising thiol groups, the one or more first reactants comprising (A) (i) at least one epoxy silane and (ii) 1,2-ethanedithiol, or (B) 3 mercaptopropyl-trimethoxysilane; and
polymerizing one or more monomers onto the intermediate product via the thiol groups to form polymer chains covalently bonded to the thiol groups, wherein said polymerizing step comprises utilizing a reaction mixture consisting of (i) the intermediate product comprising thiol groups, (ii) the one or more monomers, (iii) the bromate ion-containing salt, and (iv) deionized water.

11. The method of claim 10, wherein the bromate ion-containing salt consists of sodium bromate.

12. The method of claim 10, wherein the polymer chains comprise (i) one or more positive charges, (ii) one or more negative charges, (iii) one or more ionizable functional groups that can form a positive or negative charge via dissociation or association of an atom or an ion, or (iv) any combination of (i) to (iii).

13. The method of claim 12, wherein the support material comprises silica particles.

14. The method of claim 10, wherein the one or more first reactants comprise (i) at least one epoxy silane and (ii) 1,2-ethanedithiol.

15. The method of claim 10, wherein the one or more monomers comprise 2-acrylamido-2-methyl-1-propanesulfonic acid, vinylsulfonic acid, or any combination thereof; or 2-acrylamido-2-methyl-1-propanesulfonic acid, methacrylic acid, acrylic acid, N,N-diethylaminoethyl acrylate, (3-acrylamidopropyl)-trimethylammonium chloride, diallyldimethylammonium chloride, or any combination thereof.

16. The method of claim 15, wherein the support material comprises silica particles.

17. A method for forming chromatographic material, said method comprising:
reacting support material with one or more first reactants to form an intermediate product comprising thiol groups, the one or more first reactants comprising (A) (i) at least one epoxy silane and (ii) 1,2-ethanedithiol, or (B) 3 mercaptopropyl-trimethoxysilane; and
polymerizing one or more monomers onto the intermediate product via the thiol groups to form polymer chains covalently bonded to the thiol groups, said polymerizing step comprising utilizing a reaction mixture of (i) the intermediate product comprising thiol groups, (ii) the one or more monomers, (iii) an oxidizing agent comprising a bromate ion-containing salt, and (iv) deionized water; and the reaction mixture is free of organic solvent.

18. The method of claim 17, wherein the support material comprises particulates, fibers, plates, membranes, monoliths, or a combination thereof.

19. The method of claim 17, wherein the polymer chains comprise (i) one or more positive charges, (ii) one or more negative charges, (iii) one or more ionizable functional groups that can form a positive or negative charge via dissociation or association of an atom or an ion, or (iv) any combination of (i) to (iii).

20. The method of claim 19, wherein the support material comprises silica particles.

21. The method of claim 17, wherein the one or more monomers comprise 2-acrylamido-2-methyl-1-propanesulfonic acid, vinylsulfonic acid, or any combination thereof; or 2-acrylamido-2-methyl-1-propanesulfonic acid, methacrylic acid, acrylic acid, N,N-diethylaminoethyl acrylate, (3-acrylamidopropyl)-trimethylammonium chloride, diallyldimethylammonium chloride, or any combination thereof.

22. The method of claim 17, wherein the one or more first reactants comprise (i) at least one epoxy silane and (ii) 1,2-ethanedithiol.

23. The method of claim 22, wherein the at least one epoxy silane comprises (3-glycidoxypropyl)-trimethoxysilane.

24. The method of claim 17, wherein the one or more first reactants comprise (i) 3 mercaptopropyl-trimethoxysilane and (ii) 2-[methoxy(poly-ethyleneoxy)propyl]-trimethoxysilane.

25. The method of claim 21, wherein the support material comprises silica particles.

26. A chromatographic material formed by the method of claim 1.

27. A chromatographic material formed by the method of claim 10.

28. A chromatographic material formed by the method of claim 17.

* * * * *